(12) United States Patent
Satoshi

(10) Patent No.: US 8,026,363 B2
(45) Date of Patent: Sep. 27, 2011

(54) PROCESS FOR PRODUCING COELENTERAMIDE OR AN ANALOG THEREOF

(75) Inventor: Inouye Satoshi, Yokohama (JP)

(73) Assignee: JNC Corporation, Tokyo (JP)

( * ) Notice: Subject to any disclaimer, the term of this patent is extended or adjusted under 35 U.S.C. 154(b) by 0 days.

(21) Appl. No.: 12/656,638

(22) Filed: Feb. 5, 2010

(65) Prior Publication Data
US 2010/0249387 A1 Sep. 30, 2010

(30) Foreign Application Priority Data
Feb. 6, 2009 (JP) ................................. 2009-026757

(51) Int. Cl.
C07D 241/00 (2006.01)
(52) U.S. Cl. ...................................................... 544/336
(58) Field of Classification Search ................... 544/336
See application file for complete search history.

(56) References Cited

FOREIGN PATENT DOCUMENTS
EP 1 666 488 6/2006
GB 2 426 761 12/2006

OTHER PUBLICATIONS

Shimomura, Osamu and Katsunori Teranishi, "Light-emitters involved in the luminescence of coelenterazine", Luminescence, 2000, vol. 15, pp. 51-58.
Shimomura, Osamu and Frank H. Johnson, "Chemical Nature of the Light Emitter in Bioluminescence of Aequorin", Tetrahedron Letters, 1973, No. 31, pp. 2963-2966.
Inouye, Satoshi and Takamitsu Hosoya, "Reconstitution of blue fluorescent protein from recombinant apoaequorin and synthetic coelenteramide", Biochemical and Biophysical Research Communications, 2009, vol. 386, pp. 617-622.
Shimomura, "The Jellyfish Aequorea and Other Luminous Coelenterates", Bioluminescence: Chemical Principles and Methods, pp. 90-158, World Scientific Pub. Co., 2006.
Osamu Shimomura et al., "Extraction, Purification and Properties of Aequorin, a Bioluminescent Protein from the Luminous Hydromedusan, Aequorea", Journal of Cellular and Comparative Physiology, vol. 59, No. 3, pp. 223-240, Jun. 1962.
James F. Head et al., "The crystal structure of the photoprotein aequorin at 2.3 Å resolution", Nature, vol. 405, pp. 372-376, May 18, 2000.
Satoshi Inouye et al., "Cloning and sequence analysis of cDNA for the luminescent protein aequorin", Proc. Natl. Acad. Sci. USA, vol. 82, pp. 3154-3158, May 1985.
Osamu Shimomura et al., "Structure of the Light-Emitting Moiety of Aequorin", Biochemistry, vol. 11, No. 9, pp. 1602-1608, 1972.
Osamu Shimomura et al., "Chemical Nature of the Light Emitter in Bioluminescence of Aequorin", Tetrahedron Letters, No. 31, pp. 2963-2966, 1973.
Osamu Shimomura et al., "Regeneration of the photoprotein aequorin", Nature, vol. 256, pp. 236-238, Jul. 17, 1975.
Osamu Shimomura, "Cause of spectral variation in the luminescence of semisynthetic aequorins", Biochem. J., 306, pp. 537-543, 1995.
Satoshi Inouye, "Blue fluorescent protein from the calcium-sensitive photoprotein aequorin is a heat resistant enzyme, catalyzing the oxidation of coelenterazine", FEBS Letters, 577, pp. 105-110, 2004.
Satoshi Inouye et al., "Expression of Apoaequorin Complementary DNA in *Escherichia coli*", Biochemistry, 25, pp. 8425-8429, 1986.
Satoshi Inouye et al., "Overexpression and Purification of the Recombinant $Ca^{2+}$-Binding Protein, Apoaequorin", J. Biochem, 105, pp. 473-477, 1989.
Osamu Shimomura et al., "The in Situ Regeneration and Extraction of Recombinant Aequorin from *Escherichia coli* Cells and the Purification of Extracted Aequorin", Protein Expression and Purification, 16, pp. 91-95, 1999.
Osamu Shimomura et al., "Recombinant aequorin and recombinant semi-synthetic aequorins Cellular $Ca^{2+}$ ion indicators", Biochem. J., 270, pp. 309-312, 1990.
Sachiko Toma et al., "The crystal structures of semi-synthetic aequorins", Protein Science, 14, pp. 409-416, 2005.
Wakana Ohashi et al., "NMR Analysis of the $Mg^{2+}$-Binding Properties of Aequorin, a $Ca^{2+}$-Binding Photoprotein", J. Biochem., vol. 138, No. 5, pp. 613-620, 2005.
Satoshi Inouye et al., "Blue fluorescent protein from the calcium-sensitive photoprotein aequorin: Catalytic properties for the oxidation of coelenterazine as an oxygenase", FEBS Letters, 580, pp. 1977-1982, 2006.
Satoshi Inouye et al., "Imidazole-assisted catalysis of luminescence reaction in blue fluorescent protein from the photoprotein aequorin", Biochemical and Biophysical Research Communications, 354, pp. 650-655, 2007.

Primary Examiner — James O Wilson
Assistant Examiner — Douglas M Willis
(74) Attorney, Agent, or Firm — Wenderoth, Lind & Ponack, LLP

(57) ABSTRACT

A process for producing coelenteramide or its analog in a high yield has been desired. The invention provides a process for producing di-O-methylcoelenteramide or its analog of formula (3)

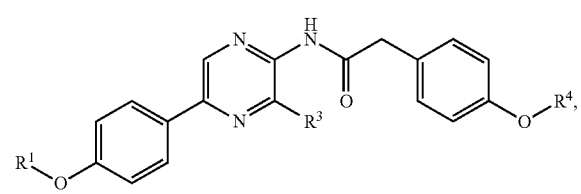

(3)

which comprises reacting O-methylcoelenteramine or its analog with 4-methoxyphenylacetyl halide or its analog. The invention also provides a process for producing coelenteramide or its analog, which comprises demethylation of di-O-methylcoelenteramide or its analog.

14 Claims, 6 Drawing Sheets

SEQUENCE LISTING

```
<160> NUMBER OF SEQ ID NOS: 14

<210> SEQ ID NO 1
<211> LENGTH: 591
<212> TYPE: DNA
<213> ORGANISM: Aequorea victoria
<220> FEATURE:
<221> NAME/KEY: CDS
<222> LOCATION: (1)..(591)

<400> SEQUENCE: 1 atg aca agc aaa caa tac tca gtc aag ctt aca tca gac ttc gac aac      48
```

```
Met Thr Ser Lys Gln Tyr Ser Val Lys Leu Thr Ser Asp Phe Asp Asn
1               5                   10                  15 cca aga tgg att gga cga cac aag cat atg ttc aat ttc ctt gat gtc         96
Pro Arg Trp Ile Gly Arg His Lys His Met Phe Asn Phe Leu Asp Val
            20                  25                  30 aac cac aat gga aaa atc tct ctt gac gag atg gtc tac aag gca tct        144
Asn His Asn Gly Lys Ile Ser Leu Asp Glu Met Val Tyr Lys Ala Ser
            35                  40                  45 gat att gtc atc aat aac ctt gga gca aca cct gag caa gcc aaa cga        192
Asp Ile Val Ile Asn Asn Leu Gly Ala Thr Pro Glu Gln Ala Lys Arg
50                  55                  60 cac aaa gat gct gta gaa gcc ttc ttc gga gga gct gga atg aaa tat        240
His Lys Asp Ala Val Glu Ala Phe Phe Gly Gly Ala Gly Met Lys Tyr
65                  70                  75                  80 ggt gtg gaa act gat tgg cct gca tat att gaa gga tgg aaa aaa ttg        288
Gly Val Glu Thr Asp Trp Pro Ala Tyr Ile Glu Gly Trp Lys Lys Leu
                85                  90                  95 gct act gat gaa ttg gag aaa tac gcc aaa aac gaa cca acg ctc atc        336
Ala Thr Asp Glu Leu Glu Lys Tyr Ala Lys Asn Glu Pro Thr Leu Ile
            100                 105                 110 cgt ata tgg ggt gat gct ttg ttt gat atc gtt gac aaa gat caa aat        384
Arg Ile Trp Gly Asp Ala Leu Phe Asp Ile Val Asp Lys Asp Gln Asn
            115                 120                 125 gga gcc att aca ctg gat gaa tgg aaa gca tac acc aaa gct gct ggt        432
Gly Ala Ile Thr Leu Asp Glu Trp Lys Ala Tyr Thr Lys Ala Ala Gly
        130                 135                 140 atc atc caa tca tca gaa gat tgc gag gaa aca ttc aga gtg tgc gat        480
Ile Ile Gln Ser Ser Glu Asp Cys Glu Glu Thr Phe Arg Val Cys Asp
145                 150                 155                 160 att gat gaa agt gga caa ctc gat gtt gat gag atg aca aga caa cat        528
Ile Asp Glu Ser Gly Gln Leu Asp Val Asp Glu Met Thr Arg Gln His
                165                 170                 175 tta gga ttt tgg tac acc atg gat cct gct tgc gaa aag ctc tac ggt        576
Leu Gly Phe Trp Tyr Thr Met Asp Pro Ala Cys Glu Lys Leu Tyr Gly
            180                 185                 190 gga gct gtc ccc taa                                                    591
Gly Ala Val Pro
        195

<210> SEQ ID NO 2
<211> LENGTH: 196
<212> TYPE: PRT
<213> ORGANISM: Aequorea victoria

<400> SEQUENCE: 2

Met Thr Ser Lys Gln Tyr Ser Val Lys Leu Thr Ser Asp Phe Asp Asn
1               5                   10                  15

Pro Arg Trp Ile Gly Arg His Lys His Met Phe Asn Phe Leu Asp Val
            20                  25                  30

Asn His Asn Gly Lys Ile Ser Leu Asp Glu Met Val Tyr Lys Ala Ser
            35                  40                  45

Asp Ile Val Ile Asn Asn Leu Gly Ala Thr Pro Glu Gln Ala Lys Arg
50                  55                  60

His Lys Asp Ala Val Glu Ala Phe Phe Gly Gly Ala Gly Met Lys Tyr
65                  70                  75                  80

Gly Val Glu Thr Asp Trp Pro Ala Tyr Ile Glu Gly Trp Lys Lys Leu
                85                  90                  95

Ala Thr Asp Glu Leu Glu Lys Tyr Ala Lys Asn Glu Pro Thr Leu Ile
            100                 105                 110
```

```
Arg Ile Trp Gly Asp Ala Leu Phe Asp Ile Val Asp Lys Asp Gln Asn
        115                 120                 125

Gly Ala Ile Thr Leu Asp Glu Trp Lys Ala Tyr Thr Lys Ala Ala Gly
    130                 135                 140

Ile Ile Gln Ser Ser Glu Asp Cys Glu Glu Thr Phe Arg Val Cys Asp
145                 150                 155                 160

Ile Asp Glu Ser Gly Gln Leu Asp Val Asp Glu Met Thr Arg Gln His
                165                 170                 175

Leu Gly Phe Trp Tyr Thr Met Asp Pro Ala Cys Glu Lys Leu Tyr Gly
            180                 185                 190

Gly Ala Val Pro
        195

<210> SEQ ID NO 3
<211> LENGTH: 597
<212> TYPE: DNA
<213> ORGANISM: Clytia gregaria
<220> FEATURE:
<221> NAME/KEY: CDS
<222> LOCATION: (1)..(597)

<400> SEQUENCE: 3 atg gct gac act gca tca aaa tac gcc gtc aaa ctc aga ccc aac ttc       48
Met Ala Asp Thr Ala Ser Lys Tyr Ala Val Lys Leu Arg Pro Asn Phe
1               5                   10                  15 gac aac cca aaa tgg gtc aac aga cac aaa ttt atg ttc aac ttt ttg       96
Asp Asn Pro Lys Trp Val Asn Arg His Lys Phe Met Phe Asn Phe Leu
                20                  25                  30 gac att aac ggc gac gga aaa atc act ttg gat gaa atc gtc tcc aaa      144
Asp Ile Asn Gly Asp Gly Lys Ile Thr Leu Asp Glu Ile Val Ser Lys
            35                  40                  45 gct tcg gat gac att tgc gcc aaa ctt gga gca aca cca gaa cag acc      192
Ala Ser Asp Asp Ile Cys Ala Lys Leu Gly Ala Thr Pro Glu Gln Thr
        50                  55                  60 aaa cgt cac cag gat gct gtc gaa gct ttc ttc aaa aag att ggt atg      240
Lys Arg His Gln Asp Ala Val Glu Ala Phe Phe Lys Lys Ile Gly Met
65                  70                  75                  80 gat tat ggt aaa gaa gtc gaa ttc cca gct ttt gtt gat gga tgg aaa      288
Asp Tyr Gly Lys Glu Val Glu Phe Pro Ala Phe Val Asp Gly Trp Lys
                85                  90                  95 gaa ctg gcc aat tat gac ttg aaa ctt tgg tct caa aac aag aaa tct      336
Glu Leu Ala Asn Tyr Asp Leu Lys Leu Trp Ser Gln Asn Lys Lys Ser
            100                 105                 110 ttg atc cgc gac tgg gga gaa gct gtt ttc gac att ttt gac aaa gac      384
Leu Ile Arg Asp Trp Gly Glu Ala Val Phe Asp Ile Phe Asp Lys Asp
        115                 120                 125 gga agt ggc tca atc agt ttg gac gaa tgg aag gct tat gga cga atc      432
Gly Ser Gly Ser Ile Ser Leu Asp Glu Trp Lys Ala Tyr Gly Arg Ile
130                 135                 140 tct gga atc tgc tca tca gac gaa gac gcc gaa aag acc ttc aaa cat      480
Ser Gly Ile Cys Ser Ser Asp Glu Asp Ala Glu Lys Thr Phe Lys His
145                 150                 155                 160 tgc gat ttg gac aac agt ggc aaa ctt gat gtt gat gag atg acc aga      528
Cys Asp Leu Asp Asn Ser Gly Lys Leu Asp Val Asp Glu Met Thr Arg
                165                 170                 175 caa cat ttg gga ttc tgg tac acc ttg gac ccc aac gct gat ggt ctt      576
Gln His Leu Gly Phe Trp Tyr Thr Leu Asp Pro Asn Ala Asp Gly Leu
            180                 185                 190 tac ggc aat ttt gtt cct taa                                          597
Tyr Gly Asn Phe Val Pro
        195
```

-continued

<210> SEQ ID NO 4
<211> LENGTH: 198
<212> TYPE: PRT
<213> ORGANISM: Clytia gregaria

<400> SEQUENCE: 4

Met Ala Asp Thr Ala Ser Lys Tyr Ala Val Lys Leu Arg Pro Asn Phe
1               5                   10                  15

Asp Asn Pro Lys Trp Val Asn Arg His Lys Phe Met Phe Asn Phe Leu
            20                  25                  30

Asp Ile Asn Gly Asp Gly Lys Ile Thr Leu Asp Glu Ile Val Ser Lys
        35                  40                  45

Ala Ser Asp Asp Ile Cys Ala Lys Leu Gly Ala Thr Pro Glu Gln Thr
    50                  55                  60

Lys Arg His Gln Asp Ala Val Glu Ala Phe Phe Lys Lys Ile Gly Met
65                  70                  75                  80

Asp Tyr Gly Lys Glu Val Glu Phe Pro Ala Phe Val Asp Gly Trp Lys
                85                  90                  95

Glu Leu Ala Asn Tyr Asp Leu Lys Leu Trp Ser Gln Asn Lys Lys Ser
            100                 105                 110

Leu Ile Arg Asp Trp Gly Glu Ala Val Phe Asp Ile Phe Asp Lys Asp
        115                 120                 125

Gly Ser Gly Ser Ile Ser Leu Asp Glu Trp Lys Ala Tyr Gly Arg Ile
    130                 135                 140

Ser Gly Ile Cys Ser Ser Asp Glu Asp Ala Glu Lys Thr Phe Lys His
145                 150                 155                 160

Cys Asp Leu Asp Asn Ser Gly Lys Leu Asp Val Asp Glu Met Thr Arg
                165                 170                 175

Gln His Leu Gly Phe Trp Tyr Thr Leu Asp Pro Asn Ala Asp Gly Leu
            180                 185                 190

Tyr Gly Asn Phe Val Pro
        195

<210> SEQ ID NO 5
<211> LENGTH: 657
<212> TYPE: DNA
<213> ORGANISM: Clytia gregaria
<220> FEATURE:
<221> NAME/KEY: CDS
<222> LOCATION: (1)..(657)

<400> SEQUENCE: 5 atg tcg gct tta gct gca aga tca aga ttg caa cgc aca gca aat ttt     48
Met Ser Ala Leu Ala Ala Arg Ser Arg Leu Gln Arg Thr Ala Asn Phe
1               5                   10                  15 cac acc agc ata ctg ttg gct aca gat tca aaa tac gcg gtc aaa ctc     96
His Thr Ser Ile Leu Leu Ala Thr Asp Ser Lys Tyr Ala Val Lys Leu
            20                  25                  30 gat cct gat ttt gca aat cca aaa tgg atc aac aga cac aaa ttt atg    144
Asp Pro Asp Phe Ala Asn Pro Lys Trp Ile Asn Arg His Lys Phe Met
        35                  40                  45 ttc aac ttt ttg gac ata aac ggt aat ggg aaa atc aca tta gat gaa    192
Phe Asn Phe Leu Asp Ile Asn Gly Asn Gly Lys Ile Thr Leu Asp Glu
    50                  55                  60 atc gtc tcc aaa gct tca gac gac att tgt gct aaa ctg gat gca aca    240
Ile Val Ser Lys Ala Ser Asp Asp Ile Cys Ala Lys Leu Asp Ala Thr
65                  70                  75                  80 cca gaa cag acc aaa cgt cac cag gat gct gtt gaa gcg ttt ttc aag    288

```
                                   Pro Glu Gln Thr Lys Arg His Gln Asp Ala Val Glu Ala Phe Phe Lys
                                                   85                  90                  95 aaa atg ggc atg gat tat ggt aaa gaa gtt gca ttc cca gaa ttt att            336
Lys Met Gly Met Asp Tyr Gly Lys Glu Val Ala Phe Pro Glu Phe Ile
                100                 105                 110 aag gga tgg gaa gag ttg gcc gaa cac gac ttg gaa ctc tgg tct caa            384
Lys Gly Trp Glu Glu Leu Ala Glu His Asp Leu Glu Leu Trp Ser Gln
            115                 120                 125 aac aaa agt aca ttg atc cgt gaa tgg gga gat gct gtt ttc gac att            432
Asn Lys Ser Thr Leu Ile Arg Glu Trp Gly Asp Ala Val Phe Asp Ile
    130                 135                 140 ttc gac aaa gac gca agt ggc tca atc agt tta gac gaa tgg aag gct            480
Phe Asp Lys Asp Ala Ser Gly Ser Ile Ser Leu Asp Glu Trp Lys Ala
145                 150                 155                 160 tac gga cga atc tct gga atc tgt cca tca gac gaa gac gct gag aag            528
Tyr Gly Arg Ile Ser Gly Ile Cys Pro Ser Asp Glu Asp Ala Glu Lys
                165                 170                 175 acg ttc aaa cat tgt gat ttg gac aac agt ggc aaa ctt gat gtt gat            576
Thr Phe Lys His Cys Asp Leu Asp Asn Ser Gly Lys Leu Asp Val Asp
                180                 185                 190 gag atg acc agg caa cat tta ggc ttc tgg tac aca ttg gat cca act            624
Glu Met Thr Arg Gln His Leu Gly Phe Trp Tyr Thr Leu Asp Pro Thr
            195                 200                 205 tct gat ggt ctt tat ggc aat ttt gtt ccc taa                                657
Ser Asp Gly Leu Tyr Gly Asn Phe Val Pro
    210                 215

<210> SEQ ID NO 6
<211> LENGTH: 218
<212> TYPE: PRT
<213> ORGANISM: Clytia gregaria

<400> SEQUENCE: 6

Met Ser Ala Leu Ala Ala Arg Ser Arg Leu Gln Arg Thr Ala Asn Phe
1               5                   10                  15

His Thr Ser Ile Leu Leu Ala Thr Asp Ser Lys Tyr Ala Val Lys Leu
                20                  25                  30

Asp Pro Asp Phe Ala Asn Pro Lys Trp Ile Asn Arg His Lys Phe Met
            35                  40                  45

Phe Asn Phe Leu Asp Ile Asn Gly Asn Gly Lys Ile Thr Leu Asp Glu
        50                  55                  60

Ile Val Ser Lys Ala Ser Asp Ile Cys Ala Lys Leu Asp Ala Thr
65                  70                  75                  80

Pro Glu Gln Thr Lys Arg His Gln Asp Ala Val Glu Ala Phe Phe Lys
                85                  90                  95

Lys Met Gly Met Asp Tyr Gly Lys Glu Val Ala Phe Pro Glu Phe Ile
                100                 105                 110

Lys Gly Trp Glu Glu Leu Ala Glu His Asp Leu Glu Leu Trp Ser Gln
            115                 120                 125

Asn Lys Ser Thr Leu Ile Arg Glu Trp Gly Asp Ala Val Phe Asp Ile
    130                 135                 140

Phe Asp Lys Asp Ala Ser Gly Ser Ile Ser Leu Asp Glu Trp Lys Ala
145                 150                 155                 160

Tyr Gly Arg Ile Ser Gly Ile Cys Pro Ser Asp Glu Asp Ala Glu Lys
                165                 170                 175

Thr Phe Lys His Cys Asp Leu Asp Asn Ser Gly Lys Leu Asp Val Asp
                180                 185                 190

Glu Met Thr Arg Gln His Leu Gly Phe Trp Tyr Thr Leu Asp Pro Thr
```

```
<210> SEQ ID NO 7
<211> LENGTH: 597
<212> TYPE: DNA
<213> ORGANISM: Mitrocoma cellularia
<220> FEATURE:
<221> NAME/KEY: CDS
<222> LOCATION: (1)..(597)

<400> SEQUENCE: 7
```

| | | | | | | | | | | | | | | | | |
|---|---|---|---|---|---|---|---|---|---|---|---|---|---|---|---|---|
| atg | tca | atg | ggc | agc | aga | tac | gca | gtc | aag | ctt | acg | act | gac | ttt | gat | 48 |
| Met | Ser | Met | Gly | Ser | Arg | Tyr | Ala | Val | Lys | Leu | Thr | Thr | Asp | Phe | Asp | |
| 1 | | | | 5 | | | | | 10 | | | | | 15 | | |
| aat | cca | aaa | tgg | att | gct | cga | cac | aag | cac | atg | ttc | aac | ttc | ctt | gac | 96 |
| Asn | Pro | Lys | Trp | Ile | Ala | Arg | His | Lys | His | Met | Phe | Asn | Phe | Leu | Asp | |
| | | | 20 | | | | | 25 | | | | | 30 | | | |
| atc | aat | tca | aat | ggc | caa | atc | aat | ctg | aat | gaa | atg | gtc | cat | aag | gct | 144 |
| Ile | Asn | Ser | Asn | Gly | Gln | Ile | Asn | Leu | Asn | Glu | Met | Val | His | Lys | Ala | |
| | 35 | | | | | 40 | | | | | 45 | | | | | |
| tca | aac | att | atc | tgc | aag | aag | ctt | gga | gca | aca | gaa | gaa | caa | acc | aaa | 192 |
| Ser | Asn | Ile | Ile | Cys | Lys | Lys | Leu | Gly | Ala | Thr | Glu | Glu | Gln | Thr | Lys | |
| 50 | | | | | 55 | | | | | 60 | | | | | | |
| cgt | cat | caa | aag | tgt | gtc | gaa | gac | ttc | ttt | ggg | gga | gct | ggt | ttg | gaa | 240 |
| Arg | His | Gln | Lys | Cys | Val | Glu | Asp | Phe | Phe | Gly | Gly | Ala | Gly | Leu | Glu | |
| 65 | | | | 70 | | | | | 75 | | | | | 80 | | |
| tat | gac | aaa | gat | acc | aca | tgg | cct | gag | tac | atc | gaa | gga | tgg | aag | agg | 288 |
| Tyr | Asp | Lys | Asp | Thr | Thr | Trp | Pro | Glu | Tyr | Ile | Glu | Gly | Trp | Lys | Arg | |
| | | | 85 | | | | | 90 | | | | | 95 | | | |
| ttg | gct | aag | act | gaa | ttg | gaa | agg | cat | tca | aag | aat | caa | gtc | aca | ttg | 336 |
| Leu | Ala | Lys | Thr | Glu | Leu | Glu | Arg | His | Ser | Lys | Asn | Gln | Val | Thr | Leu | |
| | | 100 | | | | | 105 | | | | | 110 | | | | |
| atc | cga | tta | tgg | ggt | gat | gct | ttg | ttc | gac | atc | att | gac | aaa | gat | aga | 384 |
| Ile | Arg | Leu | Trp | Gly | Asp | Ala | Leu | Phe | Asp | Ile | Ile | Asp | Lys | Asp | Arg | |
| | 115 | | | | | 120 | | | | | 125 | | | | | |
| aat | gga | tcg | gtt | tcg | tta | gac | gaa | tgg | atc | cag | tac | act | cat | tgt | gct | 432 |
| Asn | Gly | Ser | Val | Ser | Leu | Asp | Glu | Trp | Ile | Gln | Tyr | Thr | His | Cys | Ala | |
| 130 | | | | | 135 | | | | | 140 | | | | | | |
| ggc | atc | caa | cag | tca | cgt | ggg | caa | tgc | gaa | gct | aca | ttt | gca | cat | tgc | 480 |
| Gly | Ile | Gln | Gln | Ser | Arg | Gly | Gln | Cys | Glu | Ala | Thr | Phe | Ala | His | Cys | |
| 145 | | | | | 150 | | | | | 155 | | | | | 160 | |
| gat | tta | gat | ggt | gac | ggt | aaa | ctt | gat | gtg | gac | gaa | atg | aca | aga | caa | 528 |
| Asp | Leu | Asp | Gly | Asp | Gly | Lys | Leu | Asp | Val | Asp | Glu | Met | Thr | Arg | Gln | |
| | | | 165 | | | | | 170 | | | | | 175 | | | |
| cat | ttg | gga | ttt | tgg | tat | tcg | gtc | gac | cca | act | tgt | gaa | gga | ctc | tac | 576 |
| His | Leu | Gly | Phe | Trp | Tyr | Ser | Val | Asp | Pro | Thr | Cys | Glu | Gly | Leu | Tyr | |
| | | 180 | | | | | 185 | | | | | 190 | | | | |
| ggt | ggt | gct | gta | cct | tat | taa | | | | | | | | | | 597 |
| Gly | Gly | Ala | Val | Pro | Tyr | | | | | | | | | | | |
| | 195 | | | | | | | | | | | | | | | |

```
<210> SEQ ID NO 8
<211> LENGTH: 198
<212> TYPE: PRT
<213> ORGANISM: Mitrocoma cellularia

<400> SEQUENCE: 8
```

Met Ser Met Gly Ser Arg Tyr Ala Val Lys Leu Thr Thr Asp Phe Asp
1               5                   10                  15

Asn Pro Lys Trp Ile Ala Arg His Lys His Met Phe Asn Phe Leu Asp

-continued

```
                    20                  25                  30
Ile Asn Ser Asn Gly Gln Ile Asn Leu Asn Glu Met Val His Lys Ala
            35                  40                  45

Ser Asn Ile Ile Cys Lys Lys Leu Gly Ala Thr Glu Glu Gln Thr Lys
        50                  55                  60

Arg His Gln Lys Cys Val Glu Asp Phe Phe Gly Ala Gly Leu Glu
65                  70                  75                  80

Tyr Asp Lys Asp Thr Thr Trp Pro Glu Tyr Ile Glu Gly Trp Lys Arg
                85                  90                  95

Leu Ala Lys Thr Glu Leu Glu Arg His Ser Lys Asn Gln Val Thr Leu
            100                 105                 110

Ile Arg Leu Trp Gly Asp Ala Leu Phe Asp Ile Ile Asp Lys Asp Arg
        115                 120                 125

Asn Gly Ser Val Ser Leu Asp Glu Trp Ile Gln Tyr Thr His Cys Ala
    130                 135                 140

Gly Ile Gln Gln Ser Arg Gly Gln Cys Glu Ala Thr Phe Ala His Cys
145                 150                 155                 160

Asp Leu Asp Gly Asp Gly Lys Leu Asp Val Asp Glu Met Thr Arg Gln
                165                 170                 175

His Leu Gly Phe Trp Tyr Ser Val Asp Pro Thr Cys Glu Gly Leu Tyr
            180                 185                 190

Gly Gly Ala Val Pro Tyr
        195

<210> SEQ ID NO 9
<211> LENGTH: 588
<212> TYPE: DNA
<213> ORGANISM: Obelia longissima
<220> FEATURE:
<221> NAME/KEY: CDS
<222> LOCATION: (1)..(588)

<400> SEQUENCE: 9 atg tct tca aaa tac gca gtt aaa ctc aag act gac ttt gat aat cca      48
Met Ser Ser Lys Tyr Ala Val Lys Leu Lys Thr Asp Phe Asp Asn Pro
1               5                  10                  15 cga tgg atc aaa aga cac aag cac atg ttt gat ttc ctc gac atc aat      96
Arg Trp Ile Lys Arg His Lys His Met Phe Asp Phe Leu Asp Ile Asn
                20                  25                  30 gga aat gga aaa atc acc ctc gat gaa att gtg tcc aag gca tct gat     144
Gly Asn Gly Lys Ile Thr Leu Asp Glu Ile Val Ser Lys Ala Ser Asp
            35                  40                  45 gac ata tgt gcc aag ctc gaa gcc aca cca gaa caa aca aaa cgc cat     192
Asp Ile Cys Ala Lys Leu Glu Ala Thr Pro Glu Gln Thr Lys Arg His
        50                  55                  60 caa gtt tgt gtt gaa gct ttc ttt aga gga tgt gga atg gaa tat ggt     240
Gln Val Cys Val Glu Ala Phe Phe Arg Gly Cys Gly Met Glu Tyr Gly
65                  70                  75                  80 aaa gaa att gcc ttc cca caa ttc ctc gat gga tgg aaa caa ttg gcg     288
Lys Glu Ile Ala Phe Pro Gln Phe Leu Asp Gly Trp Lys Gln Leu Ala
                85                  90                  95 act tca gaa ctc aag aaa tgg gca aga aac gaa cct act ctc att cgt     336
Thr Ser Glu Leu Lys Lys Trp Ala Arg Asn Glu Pro Thr Leu Ile Arg
            100                 105                 110 gaa tgg gga gat gct gtc ttt gat att ttc gac aaa gat gga agt ggt     384
Glu Trp Gly Asp Ala Val Phe Asp Ile Phe Asp Lys Asp Gly Ser Gly
        115                 120                 125 aca atc act ttg gac gaa tgg aaa gct tat gga aaa atc tct ggt atc     432
Thr Ile Thr Leu Asp Glu Trp Lys Ala Tyr Gly Lys Ile Ser Gly Ile
```

```
                 130                 135                 140
tct cca tca caa gaa gat tgt gaa gcg aca ttt cga cat tgc gat ttg    480
Ser Pro Ser Gln Glu Asp Cys Glu Ala Thr Phe Arg His Cys Asp Leu
145                 150                 155                 160 gac aac agt ggt gac ctt gat gtt gac gag atg aca aga caa cat ctt    528
Asp Asn Ser Gly Asp Leu Asp Val Asp Glu Met Thr Arg Gln His Leu
                165                 170                 175 gga ttc tgg tac act ttg gac cca gaa gct gat ggt ctc tat ggc aac    576
Gly Phe Trp Tyr Thr Leu Asp Pro Glu Ala Asp Gly Leu Tyr Gly Asn
            180                 185                 190 gga gtt ccc taa                                                    588
Gly Val Pro
        195

<210> SEQ ID NO 10
<211> LENGTH: 195
<212> TYPE: PRT
<213> ORGANISM: Obelia longissima

<400> SEQUENCE: 10

Met Ser Ser Lys Tyr Ala Val Lys Leu Lys Thr Asp Phe Asp Asn Pro
1               5                   10                  15

Arg Trp Ile Lys Arg His Lys His Met Phe Asp Phe Leu Asp Ile Asn
            20                  25                  30

Gly Asn Gly Lys Ile Thr Leu Asp Glu Ile Val Ser Lys Ala Ser Asp
        35                  40                  45

Asp Ile Cys Ala Lys Leu Glu Ala Thr Pro Glu Gln Thr Lys Arg His
    50                  55                  60

Gln Val Cys Val Glu Ala Phe Phe Arg Gly Cys Gly Met Glu Tyr Gly
65                  70                  75                  80

Lys Glu Ile Ala Phe Pro Gln Phe Leu Asp Gly Trp Lys Gln Leu Ala
                85                  90                  95

Thr Ser Glu Leu Lys Lys Trp Ala Arg Asn Glu Pro Thr Leu Ile Arg
            100                 105                 110

Glu Trp Gly Asp Ala Val Phe Asp Ile Phe Asp Lys Asp Gly Ser Gly
        115                 120                 125

Thr Ile Thr Leu Asp Glu Trp Lys Ala Tyr Gly Lys Ile Ser Gly Ile
    130                 135                 140

Ser Pro Ser Gln Glu Asp Cys Glu Ala Thr Phe Arg His Cys Asp Leu
145                 150                 155                 160

Asp Asn Ser Gly Asp Leu Asp Val Asp Glu Met Thr Arg Gln His Leu
                165                 170                 175

Gly Phe Trp Tyr Thr Leu Asp Pro Glu Ala Asp Gly Leu Tyr Gly Asn
            180                 185                 190

Gly Val Pro
        195

<210> SEQ ID NO 11
<211> LENGTH: 627
<212> TYPE: DNA
<213> ORGANISM: Beroe abyssicola
<220> FEATURE:
<221> NAME/KEY: CDS
<222> LOCATION: (1)..(627)

<400> SEQUENCE: 11 atg act gaa cgt ctg aac gag cag aac aac gag agt tac cgc tac ctg     48
Met Thr Glu Arg Leu Asn Glu Gln Asn Asn Glu Ser Tyr Arg Tyr Leu
1               5                   10                  15
```

```
aga agc gtg gga aac cag tgg cag ttc aac gta gag gac ctc cac ccc    96
Arg Ser Val Gly Asn Gln Trp Gln Phe Asn Val Glu Asp Leu His Pro
        20                  25                  30 aag atg ttg tcc cgt ctc tac aag aga ttc gat act ttc gat cta gac    144
Lys Met Leu Ser Arg Leu Tyr Lys Arg Phe Asp Thr Phe Asp Leu Asp
    35                  40                  45 agt gac ggt aag atg gag atg gac gag gtc ttg tac tgg ccc gac agg    192
Ser Asp Gly Lys Met Glu Met Asp Glu Val Leu Tyr Trp Pro Asp Arg
50                  55                  60 atg agg cag ctg gta aac gct act gat gag cag gtt gag aag atg cgg    240
Met Arg Gln Leu Val Asn Ala Thr Asp Glu Gln Val Glu Lys Met Arg
65                  70                  75                  80 gat gct gtg aga gtt ttc ttt ttg cac aag gga gtg gag cca gta aac    288
Asp Ala Val Arg Val Phe Phe Leu His Lys Gly Val Glu Pro Val Asn
                85                  90                  95 ggt ctc ctc aga gag gac tgg gtg gaa gct aac aga gtc ttc gct gag    336
Gly Leu Leu Arg Glu Asp Trp Val Glu Ala Asn Arg Val Phe Ala Glu
            100                 105                 110 gct gag aga gaa aga gag cga cga gga gaa cct tct ctt atc gca ctt    384
Ala Glu Arg Glu Arg Glu Arg Arg Gly Glu Pro Ser Leu Ile Ala Leu
        115                 120                 125 ctc tcc aac tct tac tac gat gta ctg gat gat gac ggt gat ggt act    432
Leu Ser Asn Ser Tyr Tyr Asp Val Leu Asp Asp Asp Gly Asp Gly Thr
    130                 135                 140 gtt gac gtc gat gaa tta aag acc atg atg aaa gca ttt gat gtg ccc    480
Val Asp Val Asp Glu Leu Lys Thr Met Met Lys Ala Phe Asp Val Pro
145                 150                 155                 160 cag gaa gct gcc tac acc ttc ttc gag aag gca gac act gac aag agt    528
Gln Glu Ala Ala Tyr Thr Phe Phe Glu Lys Ala Asp Thr Asp Lys Ser
                165                 170                 175 gga aag ttg gag aga aca gaa cta gtt cat ctc ttt aga aag ttt tgg    576
Gly Lys Leu Glu Arg Thr Glu Leu Val His Leu Phe Arg Lys Phe Trp
            180                 185                 190 atg gag cct tac gat cca cag tgg gac gga gtc tac gct tat aag tac    624
Met Glu Pro Tyr Asp Pro Gln Trp Asp Gly Val Tyr Ala Tyr Lys Tyr
        195                 200                 205 taa                                                                627

<210> SEQ ID NO 12
<211> LENGTH: 208
<212> TYPE: PRT
<213> ORGANISM: Beroe abyssicola

<400> SEQUENCE: 12

Met Thr Glu Arg Leu Asn Glu Gln Asn Asn Glu Ser Tyr Arg Tyr Leu
1               5                   10                  15

Arg Ser Val Gly Asn Gln Trp Gln Phe Asn Val Glu Asp Leu His Pro
            20                  25                  30

Lys Met Leu Ser Arg Leu Tyr Lys Arg Phe Asp Thr Phe Asp Leu Asp
        35                  40                  45

Ser Asp Gly Lys Met Glu Met Asp Glu Val Leu Tyr Trp Pro Asp Arg
    50                  55                  60

Met Arg Gln Leu Val Asn Ala Thr Asp Glu Gln Val Glu Lys Met Arg
65                  70                  75                  80

Asp Ala Val Arg Val Phe Phe Leu His Lys Gly Val Glu Pro Val Asn
                85                  90                  95

Gly Leu Leu Arg Glu Asp Trp Val Glu Ala Asn Arg Val Phe Ala Glu
            100                 105                 110

Ala Glu Arg Glu Arg Glu Arg Arg Gly Glu Pro Ser Leu Ile Ala Leu
```

-continued

```
                 115                 120                 125
Leu Ser Asn Ser Tyr Tyr Asp Val Leu Asp Asp Asp Gly Asp Gly Thr
            130                 135                 140
Val Asp Val Asp Glu Leu Lys Thr Met Met Lys Ala Phe Asp Val Pro
145                 150                 155                 160
Gln Glu Ala Ala Tyr Thr Phe Phe Glu Lys Ala Asp Thr Asp Lys Ser
                165                 170                 175
Gly Lys Leu Glu Arg Thr Glu Leu Val His Leu Phe Arg Lys Phe Trp
            180                 185                 190
Met Glu Pro Tyr Asp Pro Gln Trp Asp Gly Val Tyr Ala Tyr Lys Tyr
                195                 200                 205

<210> SEQ ID NO 13
<211> LENGTH: 28
<212> TYPE: DNA
<213> ORGANISM: Artificial sequence
<220> FEATURE:
<223> OTHER INFORMATION: synthetic DNA

<400> SEQUENCE: 13
aattcccacc atcaccatca ccatggta                                    28

<210> SEQ ID NO 14
<211> LENGTH: 28
<212> TYPE: DNA
<213> ORGANISM: Artificial sequence
<220> FEATURE:
<223> OTHER INFORMATION: synthetic DNA

<400> SEQUENCE: 14
agcttaccat ggtgatggtg atggtggg                                    28
```

PROCESS FOR PRODUCING COELENTERAMIDE OR AN ANALOG THEREOF

TECHNICAL FIELD

The present invention relates to a process for producing coelenteramide or an analogous compound thereof, a process for producing a green fluorescent protein (gFP), and the like.

BACKGROUND OF THE INVENTION

A calcium-binding photoprotein is one of the proteins responsible for bioluminescence. This photoprotein instantaneously emits a flash of light upon specific interaction with $Ca^{2+}$. The calcium-binding photoprotein is a complex of a protein having the catalytic function of oxygenation and the peroxide of a luciferin as a luminescence substrate. In the calcium-binding photoprotein, the protein having the catalytic function of oxygenation is called an apoprotein (e.g., apoaequorin). The peroxide of a luciferin is 2-hydroperoxycoelenterazine. Such known calcium-binding photoproteins are those derived from coelenterates, specifically including aequorin, clytin-I, clytin-H, mitrocomin, obelin, etc.

Among them, aequorin is a photoprotein isolated from the luminous jellyfish *Aequorea aequorea* (1: Shimomura, In: *Bioluminescence, Chemical Principles and Methods*, (2006) pp 90-158, World Scientific Pub. Co.; 2: Shimomura et al., (1962) *J. Cell. Comp. Physiol.* 59, pp 223-240). This aequorin is a non-covalent complex of apoaequorin (21.4 kDa) and a hydroperoxide of coelenterazine (3: Head et al., (2000) *Nature*, 405 372-376). Apoaequorin is a single polypeptide composed of 189 amino acid residues with 3 EF hand motifs characteristic of $Ca^{2+}$-binding site (4: Inouye et al., (1985) *Proc. Natl. Acad. Sci. USA.* 82, 3154-3158). In the presence of $Ca^{2+}$, aequorin emits blue light ($\lambda_{max}$=~460 nm) by an intramolecular reaction and decomposes itself into apoaequorin, coelenteramide and $CO_2$ (5: Shimomura & Johnson (1972) *Biochemistry* 11, 1602-1608; 6: Shimomura & Johnson (1973) *Tetrahedron Lett.* 2963-2966). The complex of $Ca^{2+}$-bound apoaequorin with coelenteramide obtained by this decomposition is known as blue fluorescent protein (BFP) (7: Shimomura & Johnson (1975) *Nature* 256, 236-238).

The fluorescence emission spectrum of BFP is the same as bioluminescence spectrum of aequorin (8: Shimomura, *Biochem. J.* 306 (1995) 537-543; 9: Inouye, *FEBS Lett* 577 (2004) 105-110). Recombinant apoaequorin prepared from *E. coli* can be regenerated into aequorin by incubation with coelenterazine and molecular oxygen in the presence of EDTA and a reducing agent (10: Inouye et al., (1986) *Biochemistry* 25: 8425-8429; 11: Inouye et al., (1989) *J. Biochem.*, 105, 473-477). Recombinant aequorin is highly purified (12: Shimomura & Inouye (1999) *Protein Express. Purif.* 16, 91-95). Recombinant aequorin has identical luminescence properties to those of native aequorin (13: Shimomura et al., (1990) *Biochem. J.* 270 309-312). The crystal structures of aequorin and semi-synthetic aequorin were determined (3: Head et al., *Nature*, 405 (2000) 372-376; 14: Toma et al., (2005) *Protein Science* 14:409-416) and the $Mg^{2+}$binding properties of aequorin to EF hand motifs were also examined by NMR spectroscopy (15: Ohashi et al., (2005) *J. Biochem.* 138: 613-620).

Recently, BFP was quantitatively prepared from the purified recombinant aequorin (9: Inouye, *FEBS Lett.* 577 (2004) 105-110; 16: Inouye & Sasaki, *FEBS Lett.* 580 (2006) 1977-1982). BFP was found to have a substantial luminescence activity, catalyzing the oxidation of coelenterazine like a luciferase. The luminescence intensity of BFP is about 10 times higher than that of $Ca^{2+}$-bound apoaequorin (9: Inouye *FEBS Lett* 577 (2004) 105-110). That is, BFP is a new bifunctional protein having both fluorescence and luciferase activities. Furthermore, by treatment with EDTA, BFP is converted into a green fluorescent protein (gFP) showing the maximum fluorescence emission peak at about 470 nm. gFP is a non-covalent complex of apoaequorin and coelenteramide and may reconstitute aequorin by incubation with coelenterazine at 25° C. in the absence of reducing reagents (9: Inouye, *FEBS Lett.* 577 (2004) 105-110). By incubation of various coelenterazine analogs with BFP or gFP in the presence of EDTA and dithiothreitol (DTT), semi-synthetic aequorin may also be prepared (16: Inouye et al. & Sasaki, *FEBS Lett.* 580 (2006) 1977-1982). Moreover, the luminescence activity of BFP as a luciferase is stimulated by adding imidazole at concentrations of 30 to 300 mM using coelenterazine and its analog as substrates (17: Inouye & Sasaki (2007) *Biochem. Biophys. Res. Commun.* 354: 650-655). However, the protein catalytic domains or amino acid residues for the oxygen addition to coelenterazine, which are important basic information for developing the applications of BFP and gFP, remain unknown. In solving these problems and developing the applications, it is required to easily prepare BFP and gFP of several ten milligrams. Put otherwise, it is essential to establish a process for preparing highly purified gFP from apoaequorin and coelenteramide and converting gFP into BFP.

Turning now to the production of coelenteramide, which is the starting material for producing BFP and gFP, there is known a process for producing coelenteramide, which comprises reacting the compound shown by formula below:

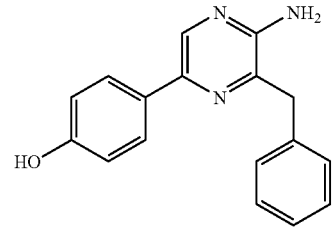

with p-hydroxyphenylacetic acid shown by formula below:

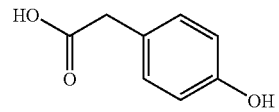

(6: Shimomura & Johnson, *Tetrahedron Lett.* (1973) 2963-2966). According to this process, the yield of coelenteramide is approximately 50%.

1. Shimomura, In: Bioluminescence, Chemical principles and methods (2006) pp 90-158, World Scientific Pub. Co.
2. Shimomura et al., (1962) *J. Cell. Comp. Physiol.* 59, pp 223-240
3. Head et al., (2000) *Nature*, 405, 372-376
4. Inouye et al., (1985) *Proc. Natl. Acad. Sci. USA.* 82, 3154-3158
5. Shimomura & Johnson (1972) *Biochemistry* 11, 1602-1608
6. Shimomura & Johnson (1973) *Tetrahedron Lett.* 2963-2966
7. Shimomura & Johnson (1975) *Nature* 256, 236-238
8. Shimomura, (1995) *Biochem. J.* 306, 537-543
9. Inouye, (2004) *FEBS Lett.* 577, 105-110
10. Inouye et al., (1986) *Biochemistry* 25, 8425-8429
11. Inouye et al., (1989) *J. Biochem.*, 105 473-477
12. Shimomura & Inouye (1999) *Protein Express. Purif.* 16, 91-95
13. Shimomura et al., (1990) *Biochem. J.* 270, 309-312

14. Toma et al., (2005) *Protein Science* 14, 409-416
15. Ohashi et al., (2005) *J. Biochem.* 138, 613-620
16. Inouye & Sasaki, (2006) *FEBS Lett.* 580, 1977-1982
17. Inouye & Sasaki, (2007) *Biochem. Biophys. Res. Commun.* 354, 650-655

SUMMARY OF THE INVENTION

Under the foregoing circumstances, a process for producing coelenteramide or its analogs in a high yield, and the like, have been desired.

In order to solve the above problems, the present inventors have made extensive investigations and, as a result, have established a novel synthetic pathway to synthesize coelenteramide from O-methylcoelenteramine via di-O-methylcoelenteramide and have come to accomplish the present invention.

That is, the present invention provides a process for producing coelenteramide or its analogs shown below, and the like.

(1) A process for producing a compound represented by general formula (3) below:

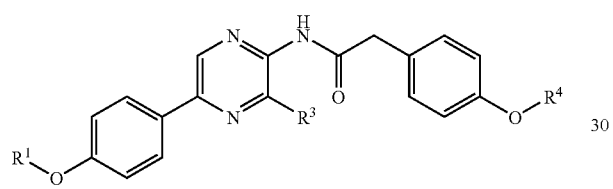

(3)

(wherein,
$R^1$ represents an alkyl having 1 to 3 carbon atoms or an arylalkyl having 7 to 10 carbon atoms,
$R^3$ represents an alkyl having 1 to 7 carbon atoms which may optionally be substituted with an alicyclic group, an alicyclic group or an arylalkyl having 7 to 10 carbon atoms, and,
$R^4$ represents an alkyl having 1 to 3 carbon atoms or an arylalkyl having 7 to 10 carbon atoms), which comprises reacting a compound represented by general formula (1) below:

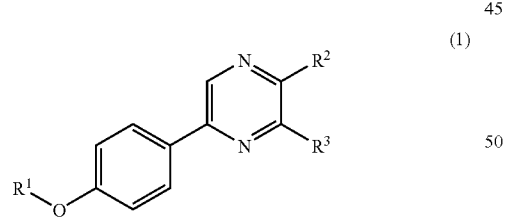

(1)

(wherein $R^1$ and $R^3$ have the same significance as defined above, and, $R^2$ is amino) with a compound represented by general formula (2) below:

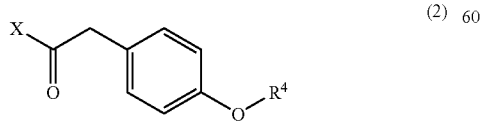

(2)

(wherein X is a splitting-off group and $R^4$ has the same significance as defined above).

(2) The process according to (1) above, wherein in general formula (1), $R^1$ is methyl, ethyl, propyl, isopropyl, benzyl, α-methylbenzyl, phenethyl, 3-phenylpropyl or 4-phenylbutyl.

(3) The process according to (1) or (2) above, wherein in general formula (1), $R^3$ is methyl, ethyl, propyl, isopropyl, butyl, isobutyl, s-butyl, t-butyl, pentyl, isopentyl, neopentyl, t-pentyl, hexyl, heptyl, cyclopropylmethyl, cyclobutylmethyl, cyclopentylmethyl, cyclohexylmethyl, cyclopropyl, cyclobutyl, cyclopentyl, cyclohexyl, α-methylbenzyl, phenethyl, 3-phenylpropyl or 4-phenylbutyl.

(4) The process according to any one of (1) through (3) above, wherein in general formula (2), X is chlorine, bromine, iodine, methanesulfonyloxy, benzenesulfonyloxy, toluenesulfonyloxy or (4-$R^4$O)$C_6H_4$CCOO— (wherein $R^4$ has the same significance as defined above).

(5) The process according to any one of (1) through (4) above, wherein in general formula (2), $R^4$ is methyl, ethyl, propyl, isopropyl, benzyl, α-methylbenzyl, phenethyl, 3-phenylpropyl or 4-phenylbutyl.

(6) The process according to any one of (1) to (5) above, wherein the compound represented by general formula (1) is selected from the group consisting of the following compounds.

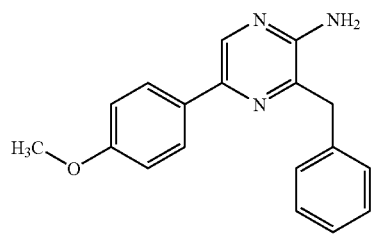

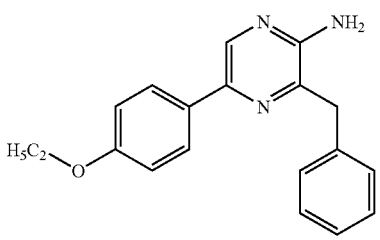

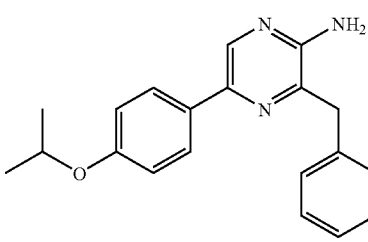

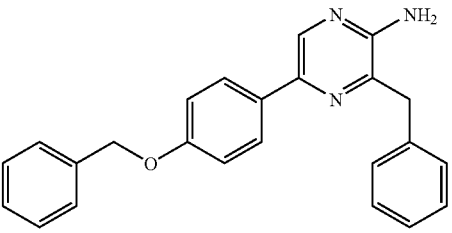

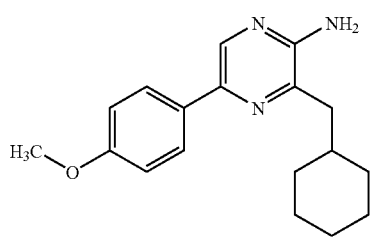

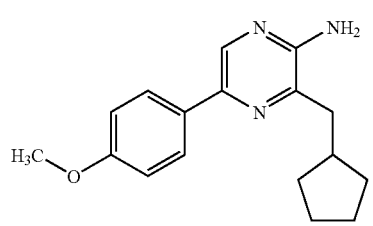

(7) The process according to any one of (1) to (6) above, wherein the compound represented by general formula (2) is selected from the group consisting of the following compounds.

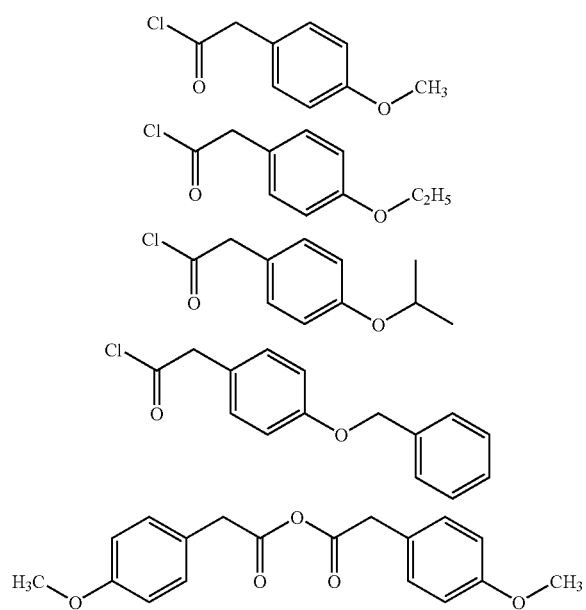

(8) A process for producing the compound represented by formula below:

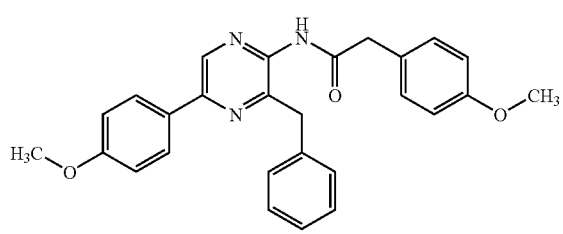

which comprises reacting the compound represented by formula below:

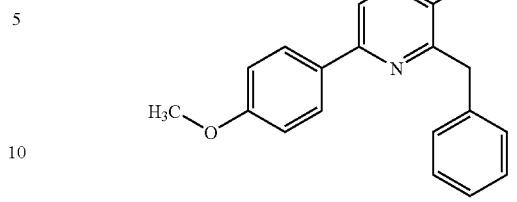

with the compound represented by formula below.

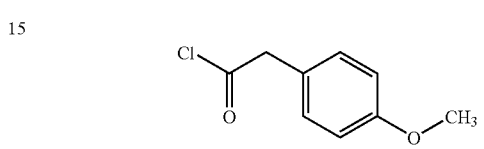

(9) A compound represented by general formula (3) below:

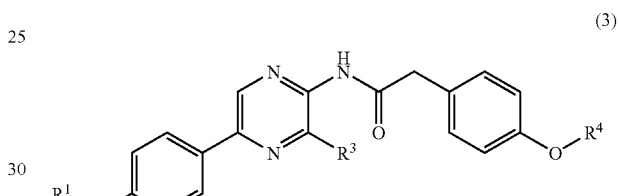

(wherein,
$R^1$ represents an alkyl having 1 to 3 carbon atoms or an arylalkyl having 7 to 10 carbon atoms,
$R^3$ represents an alkyl having 1 to 7 carbon atoms which may optionally be substituted with an alicyclic group, an alicyclic group or an arylalkyl having 7 to 10 carbon atoms, and,
$R^4$ represents an alkyl having 1 to 3 carbon atoms or an arylalkyl having 7 to 10 carbon atoms).

(10) The compound represented by formula below.

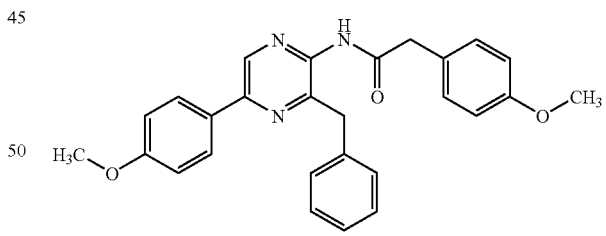

(11) A process for producing a compound represented by general formula (4) below:

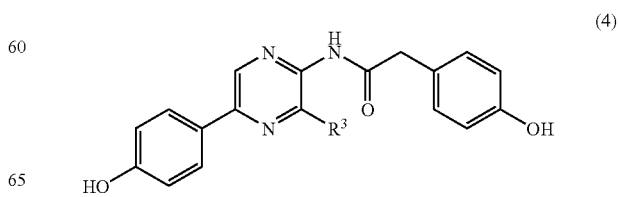

(wherein R³ represents an alkyl having 1 to 7 carbon atoms which may optionally be substituted with an alicyclic group, an alicyclic group or an arylalkyl having 7 to 10 carbon atoms),
which comprises splitting-off a group shown by R¹ (wherein R¹ represents an alkyl having 1 to 3 carbon atoms or an arylalkyl having 7 to 10 carbon atoms) and a group shown by R⁴ (wherein R⁴ represents an alkyl having 1 to 3 carbon atoms or an arylalkyl having 7 to 10 carbon atoms) from a compound represented by general formula (3) below:

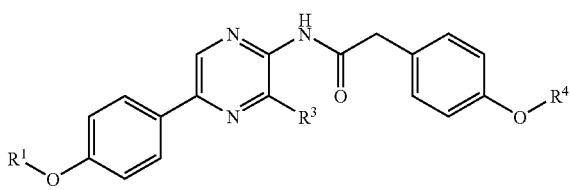

(3)

(wherein R¹, R³ and R⁴ have the same significance as defined above).

(12) The process according to (11) above, wherein in general formula (3), R¹ is methyl, ethyl, propyl, isopropyl, benzyl, α-methylbenzyl, phenethyl, 3-phenylpropyl or 4-phenylbutyl.

(13) The process according to (11) or (12) above, wherein in general formula (3), R³ is methyl, ethyl, propyl, isopropyl, butyl, isobutyl, s-butyl, t-butyl, pentyl, isopentyl, neopentyl, t-pentyl, hexyl, heptyl, cyclopropylmethyl, cyclobutylmethyl, cyclopentylmethyl, cyclohexylmethyl, cyclopropyl, cyclobutyl, cyclopentyl, cyclohexyl, α-methylbenzyl, phenethyl, 3-phenylpropyl or 4-phenylbutyl.

(14) The process according to any one of (11) to (13) above, wherein in general formula (3), R⁴ is methyl, ethyl, propyl, isopropyl, benzyl, α-methylbenzyl, phenethyl, 3-phenylpropyl or 4-phenylbutyl.

(15) The process according to any one of (11) to (14) above, wherein the compound represented by general formula (3) is selected from the group consisting of the following compounds.

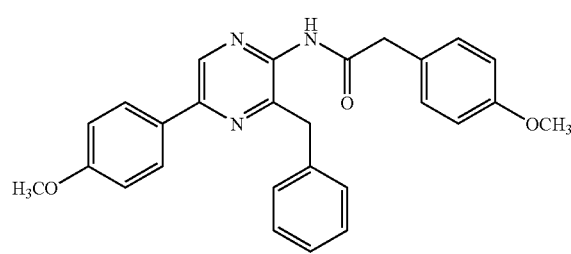
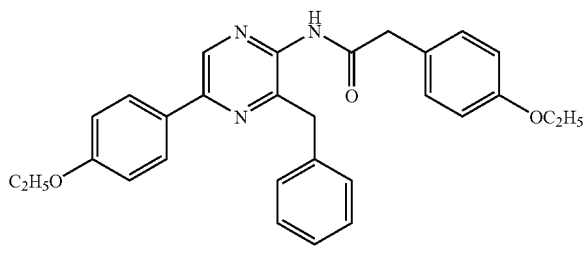
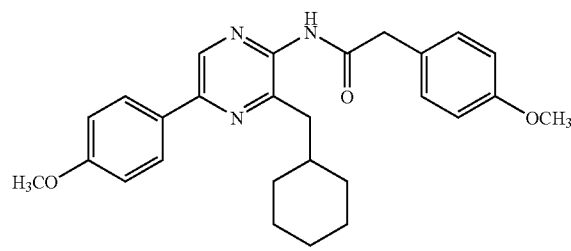
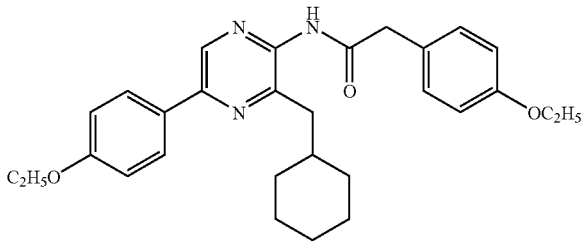
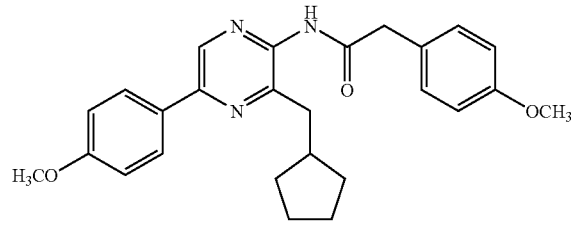
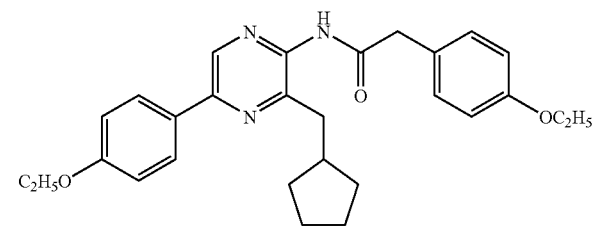
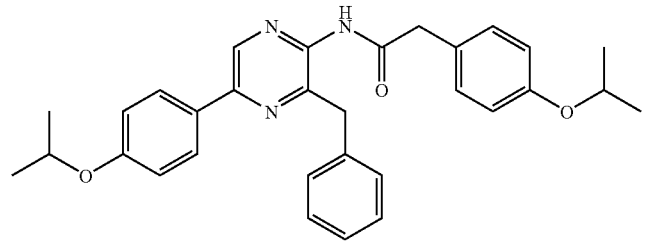

-continued
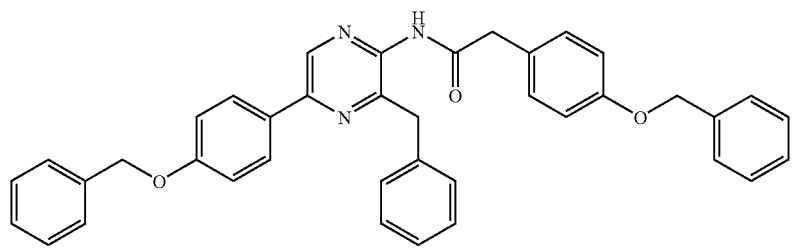
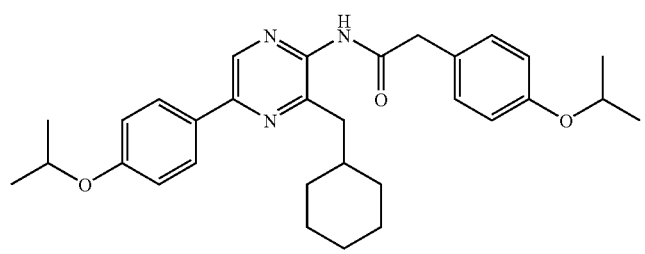
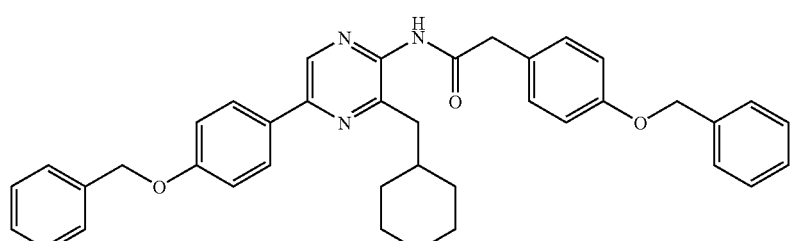
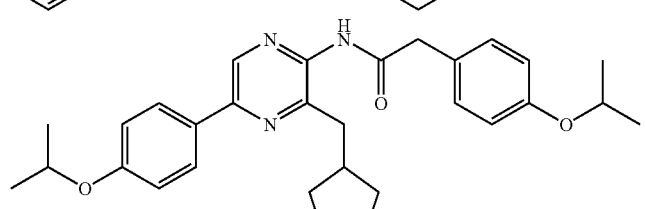
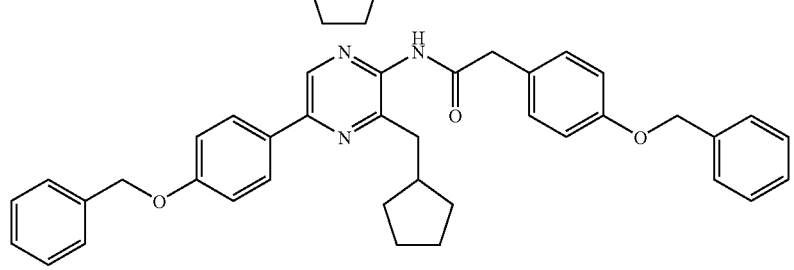
(16) A process for producing the compound represented by formula below:
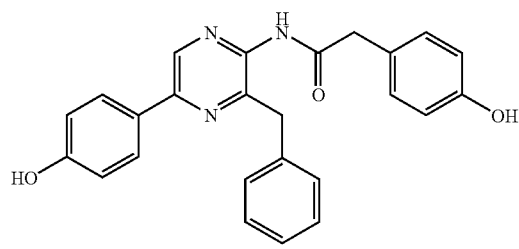
which comprises splitting off methyl from the compound represented by formula below:
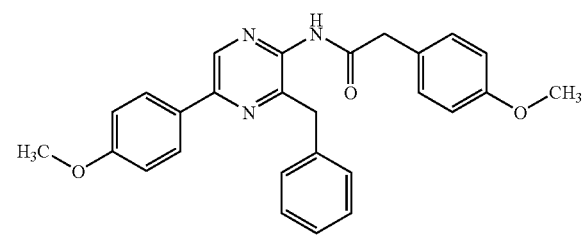

(17) A process for producing a green fluorescent protein (gFP), which comprises reacting a compound represented by general formula (4) below:

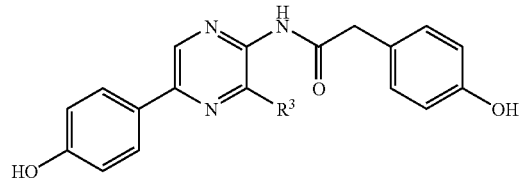

(4)

(wherein $R^3$ represents an alkyl having 1 to 7 carbon atoms which may optionally be substituted with an alicyclic group, an alicyclic group or an arylalkyl having 7 to 10 carbon atoms), with the apoprotein of a calcium-binding photoprotein in the presence of a chelating agent for sequestering a calcium ion or a divalent or trivalent ion substitutable for the calcium ion.

(18) A process for producing a green fluorescent protein (gFP), which comprises reacting the compound represented by formula below:

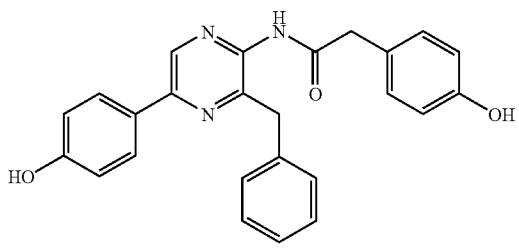

with apoaequorin in the presence of a chelating agent for sequestering a calcium ion or a divalent or trivalent ion substitutable for the calcium ion.

(19) The process according to (17) or (18) above, wherein the reaction is carried out in the presence of a reducing agent.

(20) A process for producing a blue fluorescent protein (BFP), which comprises the steps of: reacting a compound represented by general formula (1) below:

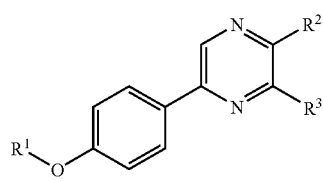

(1)

(wherein,
$R^1$ represents an alkyl having 1 to 3 carbon atoms or an arylalkyl having 7 to 10 carbon atoms,
$R^2$ is amino, and,
$R^3$ represents an alkyl having 1 to 7 carbon atoms which may optionally be substituted with an alicyclic group, an alicyclic group or an arylalkyl having 7 to 10 carbon atoms), with a compound represented by general formula (2) below:

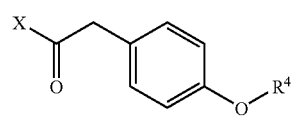

(2)

(wherein,
X is a splitting off group and,
$R^4$ represents an alkyl having 1 to 3 carbon atoms or an arylalkyl having 7 to 10 carbon atoms)
to produce a compound represented by general formula (3) below:

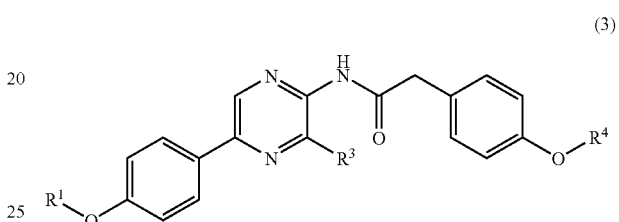

(3)

(wherein $R^1$, $R^3$ and $R^4$ have the same significance as defined above), and, reacting the compound represented by general formula (3) with the apoprotein of a calcium-binding photoprotein, in the presence of a calcium ion or a divalent or trivalent ion substitutable for the calcium ion.

According to the process for producing coelenteramide or its analogs in an embodiment of the present invention, coelenteramide or its analogs can be produced in a high yield as compared to conventional processes. According to another embodiment of the present invention, gFP can be prepared directly from apoaequorin in a simple manner.

Figure 1:
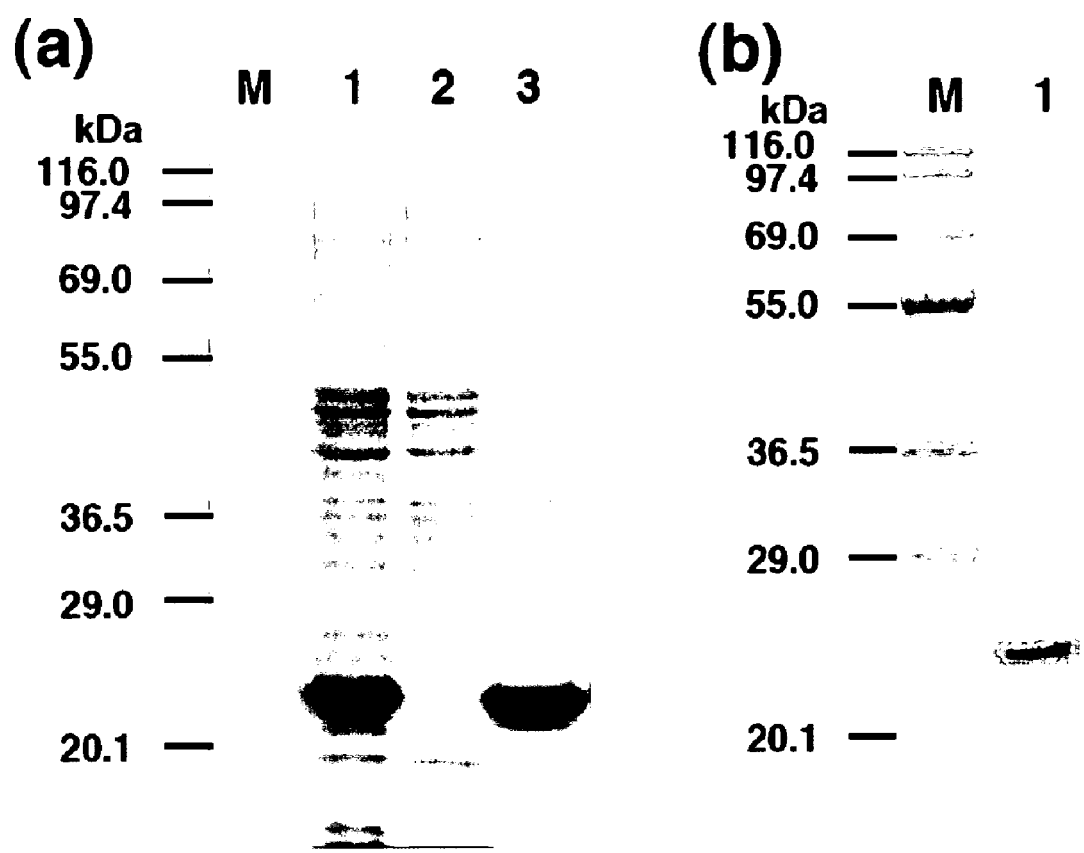
FIG. 1 shows SDS-PAGE analysis of the protein at each step of apoaequorin purification.

(a) Each step of apoaequorin purification using a nickel chelate column. Lane M: molecular weight marker (TEFCO); β-galactosidase (116 kDa), phosphorylase b (97.4 kDa), bovine serum albumin (69.0 kDa), glutamate dehydrogenase (55.0 kDa), lactate dehydrogenase (36.5 kDa), carbonic anhydrase (29.0 kDa) and trypsin inhibitor (20.1 kDa). Lane 1: the supernatant (20 μl) obtained from the crude extract after being subjected to 12,000 g. Lane 2: fraction (20 μl) obtained by washing the nickel chelate column with 50 mM Tris-HCl (pH 7.6). Lane 3: fraction (20 μl) eluted from the nickel chelate column using 50 mM Tris-HCl (pH 7.6) containing 0.1M imidazole.

(b) Purification of apoaequorin by treatment with 0.1M acetic acid. Lane M: molecular weight marker (TEFCO). Lane 1: purified apoaequorin (5 μg).

Figure 2:
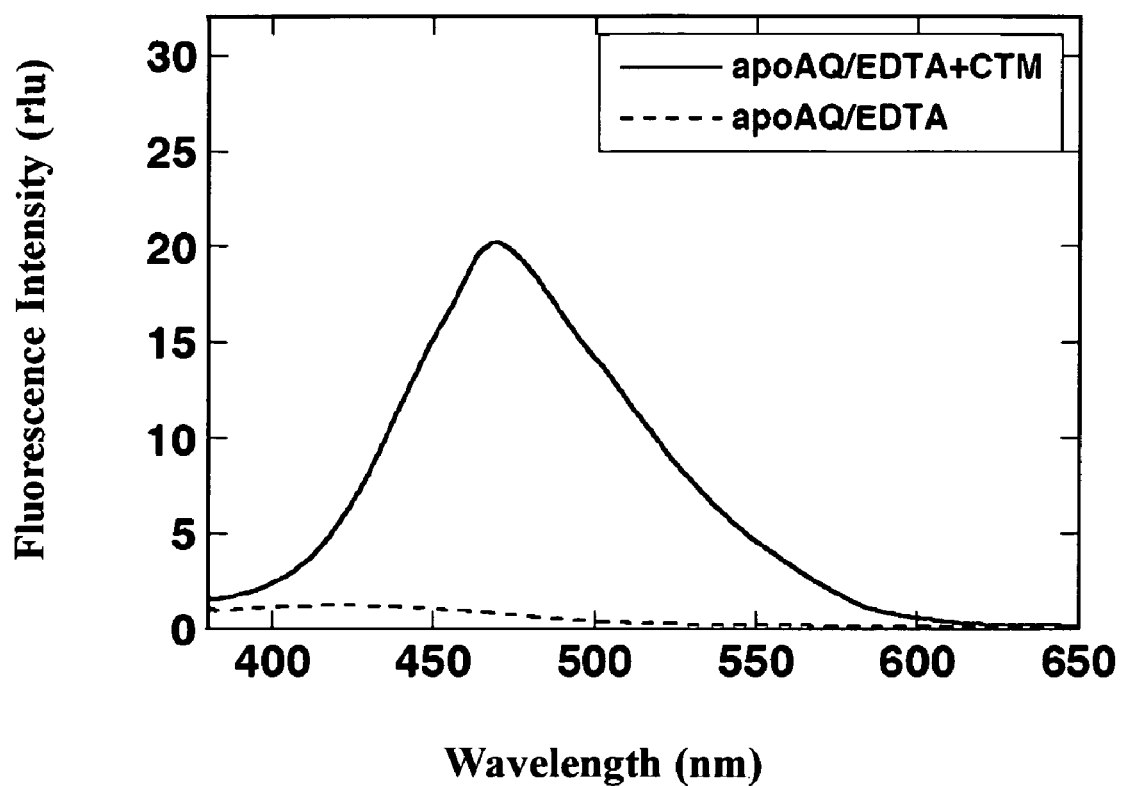

FIG. 2 shows the fluorescence spectrum of reconstituted syn-gFP obtained by incubation of apoaequorin with coelenteramide under reducing conditions.

The fluorescence spectrum was obtained by excitation at 335 nm after incubation of the purified recombinant apoaequorin (50 μg) with coelenteramide (1.2 μg dissolved in 1 μl of methanol) at 4° C. for 16 hours in 1 ml of 50 mM Tris-HCl (pH 7.6) containing 1 mM DTT in the presence of 10 mM EDTA.

Figure 3:
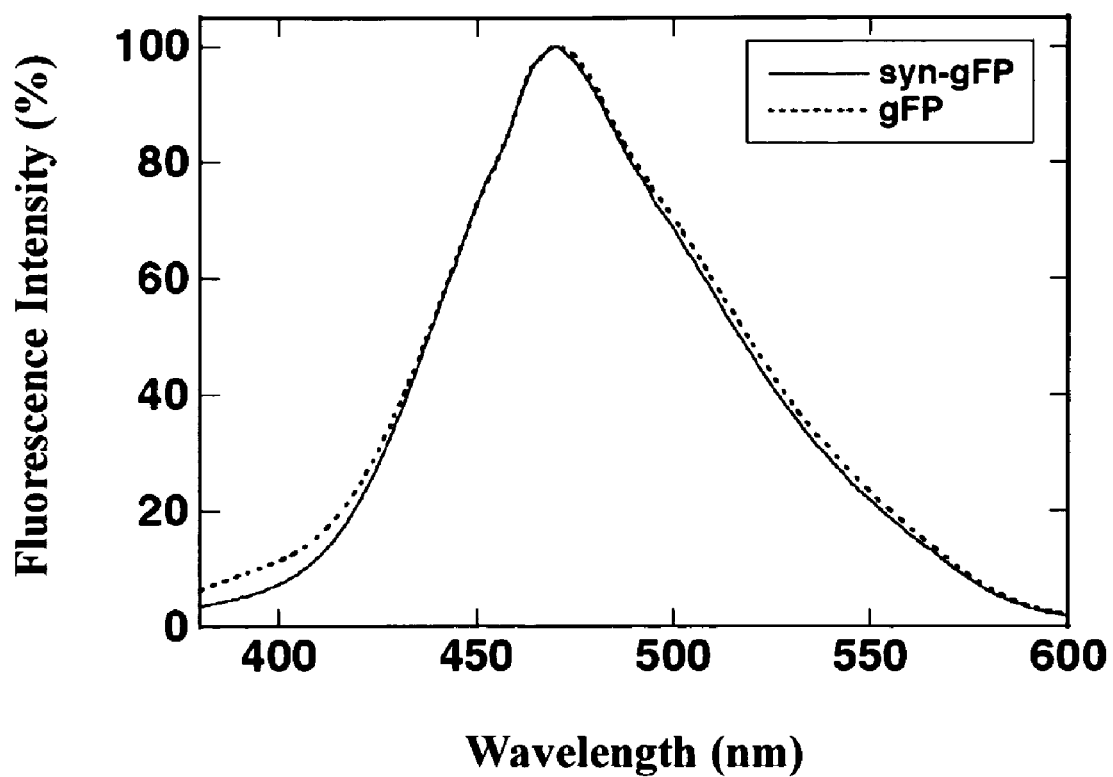

FIG. 3 shows a comparison of the fluorescence spectra between syn-gFP and gFP.

Figure 4:
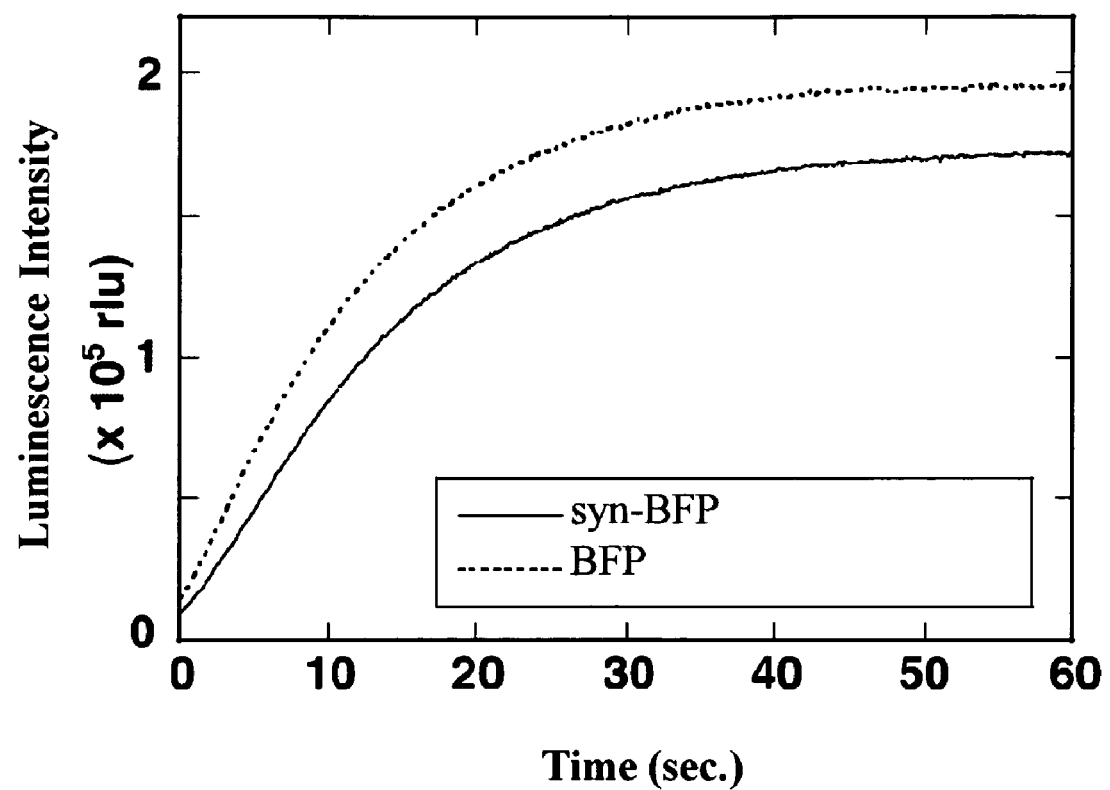

FIG. 4 shows luminescence patterns of syn-BFP and BFP using coelenterazine as a substrate.

Figure 5:
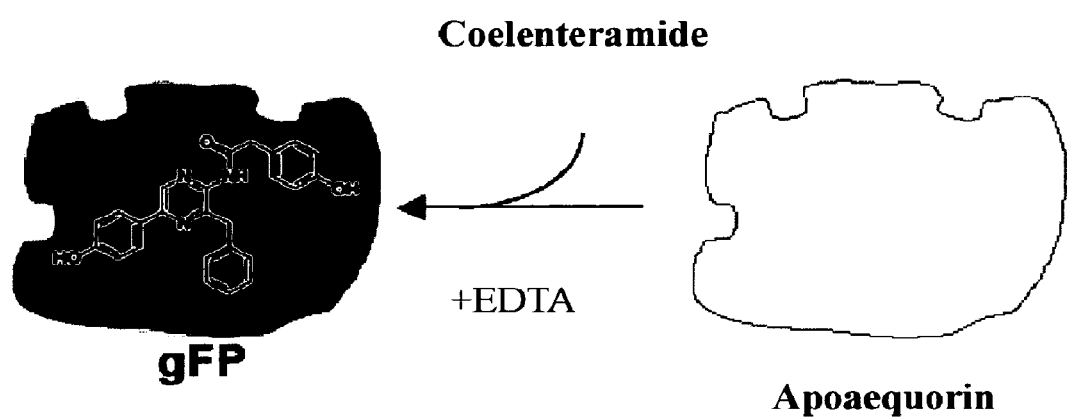

FIG. 5 shows an embodiment of the process for producing gFP in accordance with the present invention.

Figure 6:
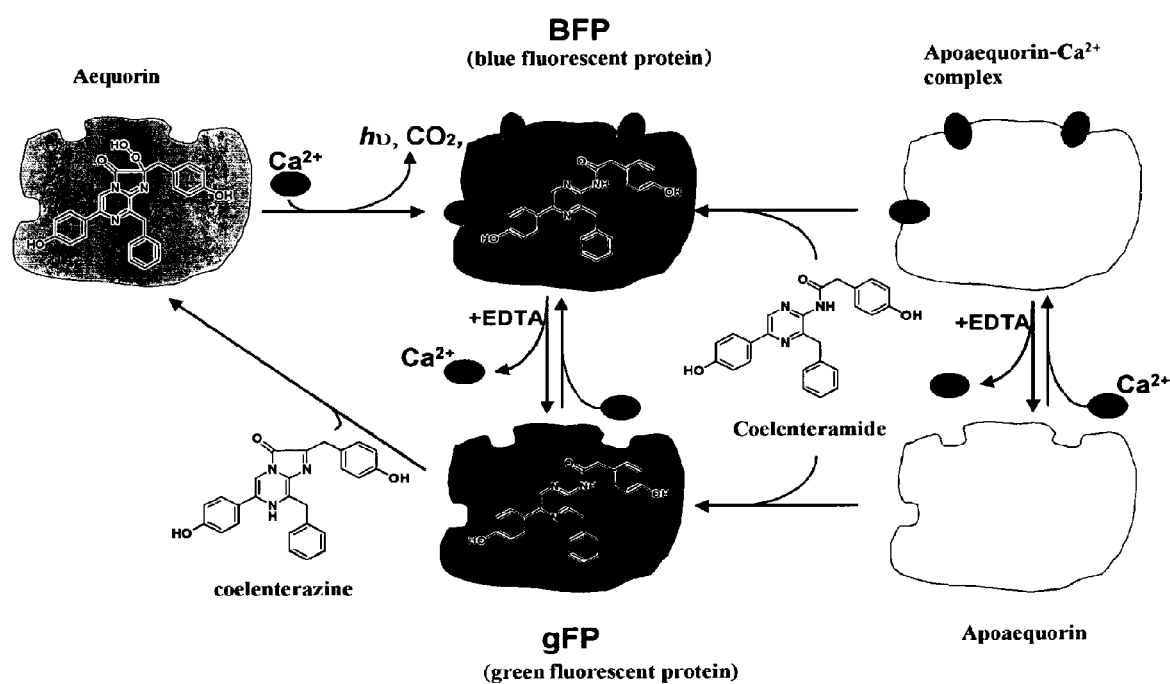

FIG. 6 shows the scheme for producing BFP, gFP, aequorin, etc. from the coelenteramide produced by the process of the present invention.

DESCRIPTION OF THE PREFERRED EMBODIMENT

Hereinafter, the present invention will be described in detail.

1. Process for Producing Coelenteramide or its Analog

According to the present invention, coelenteramide or its analogs are produced from O-methylcoelenteramine or its analogs via di-O-methylcoelenteramide or its analogs. In some embodiments of the present invention directed to the process for producing coelenteramide or its analogs, the yield prior to purification of coelenteramide or its analogs from O-methylcoelenteramine or its analogs is higher than that of conventional production processes, for example, 55% or more, 60% or more, 65% or more, or 70% or more.

1.1. Production of di-O-methylcoelenteramide or its Analogs

The present invention provides di-O-methylcoelenteramide or its analogs (the compounds represented by general formula (3)). More specifically, the present invention provides the compound represented by general formula (3) below:

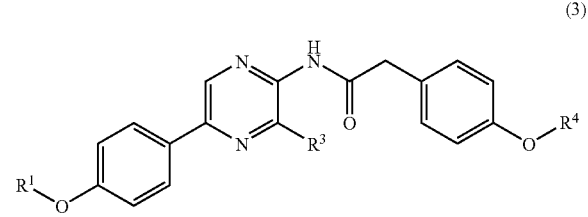

(3)

(wherein, $R^1$ represents an alkyl having 1 to 3 carbon atoms or an arylalkyl having 7 to 10 carbon atoms, $R^3$ represents an alkyl having 1 to 7 carbon atoms which may optionally be substituted with an alicyclic group, an alicyclic group or an arylalkyl having 7 to 10 carbon atoms, and, $R^4$ represents an alkyl having 1 to 3 carbon atoms or an arylalkyl having 7 to 10 carbon atoms).

In general formula (3), examples of the alkyl having 1 to 3 carbon atoms, which is shown by $R^1$, include methyl, ethyl, propyl and isopropyl. Examples of the arylalkyl having 7 to 10 carbon atoms, which is shown by $R^1$, include benzyl, α-methylbenzyl, phenethyl, 3-phenylpropyl and 4-phenylbutyl. In some embodiments of the present invention, $R^1$ is methyl, ethyl, propyl, isopropyl, benzyl, α-methylbenzyl, phenethyl, 3-phenylpropyl or 4-phenylbutyl. Preferably, $R^1$ is methyl, ethyl, isopropyl or benzyl.

In general formula (3), examples of the alkyl having 1 to 7 carbon atoms which may optionally be substituted with an alicyclic group, which is shown by $R^3$, include methyl, ethyl, propyl, isopropyl, butyl, isobutyl, s-butyl, t-butyl, pentyl, isopentyl, neopentyl, t-pentyl, hexyl, heptyl, cyclopropylmethyl, cyclobutylmethyl, cyclopentylmethyl and cyclohexylmethyl. Examples of the alicyclic group shown by $R^3$ include cyclopropyl, cyclobutyl, cyclopentyl and cyclohexyl. Examples of the arylalkyl having 7 to 10 carbon atoms, which is shown by $R^3$, include benzyl, α-methylbenzyl, phenethyl, 3-phenylpropyl and 4-phenylbutyl. In some embodiments of the present invention, $R^3$ is methyl, ethyl, propyl, isopropyl, butyl, isobutyl, s-butyl, t-butyl, pentyl, isopentyl, neopentyl, t-pentyl, hexyl, heptyl, cyclopropylmethyl, cyclobutylmethyl, cyclopentylmethyl, cyclohexylmethyl, cyclopropyl, cyclobutyl, cyclopentyl, cyclohexyl, α-methylbenzyl, phenethyl, 3-phenylpropyl or 4-phenylbutyl. Preferably, $R^3$ is cyclohexylmethyl, cyclopentylmethyl or benzyl.

In general formula (3), examples of the alkyl having 1 to 3 carbon atoms, which is shown by $R^4$, include methyl, ethyl, propyl or isopropyl. Examples of the arylalkyl having 7 to 10 carbon atoms, which is shown by $R^4$, include benzyl, α-methylbenzyl, phenethyl, 3-phenylpropyl and 4-phenylbutyl. In some embodiments of the present invention, $R^4$ is methyl, ethyl, propyl, isopropyl, benzyl, α-methylbenzyl, phenethyl, 3-phenylpropyl or 4-phenylbutyl. Preferably, $R^4$ is methyl, ethyl, isopropyl or benzyl.

In some embodiments of the present invention, the di-O-methylcoelenteramide or its analog represented by general formula (3) above includes, for example, a compound selected from the group consisting of the compounds described below.

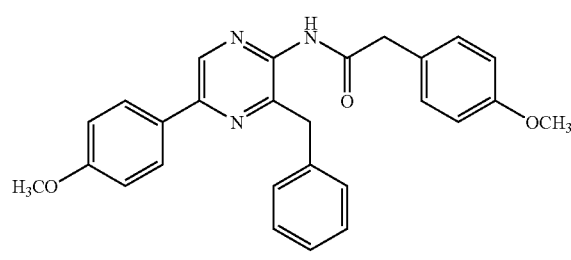

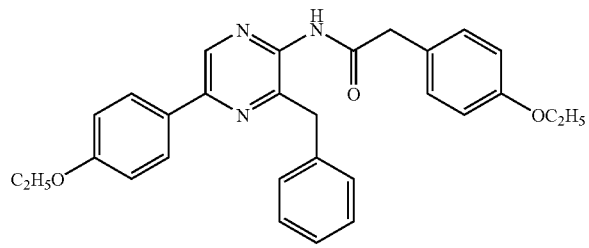

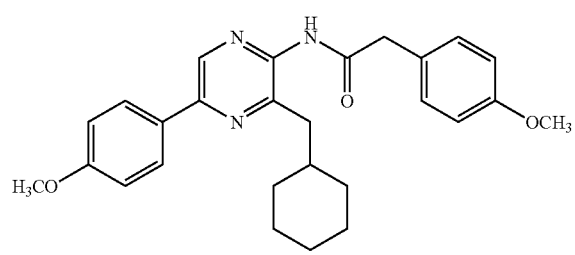

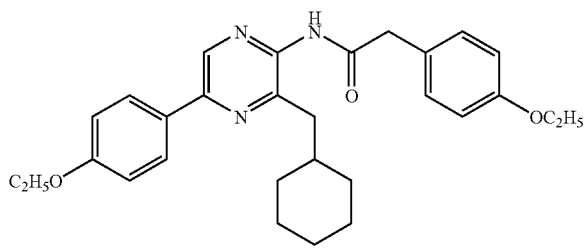

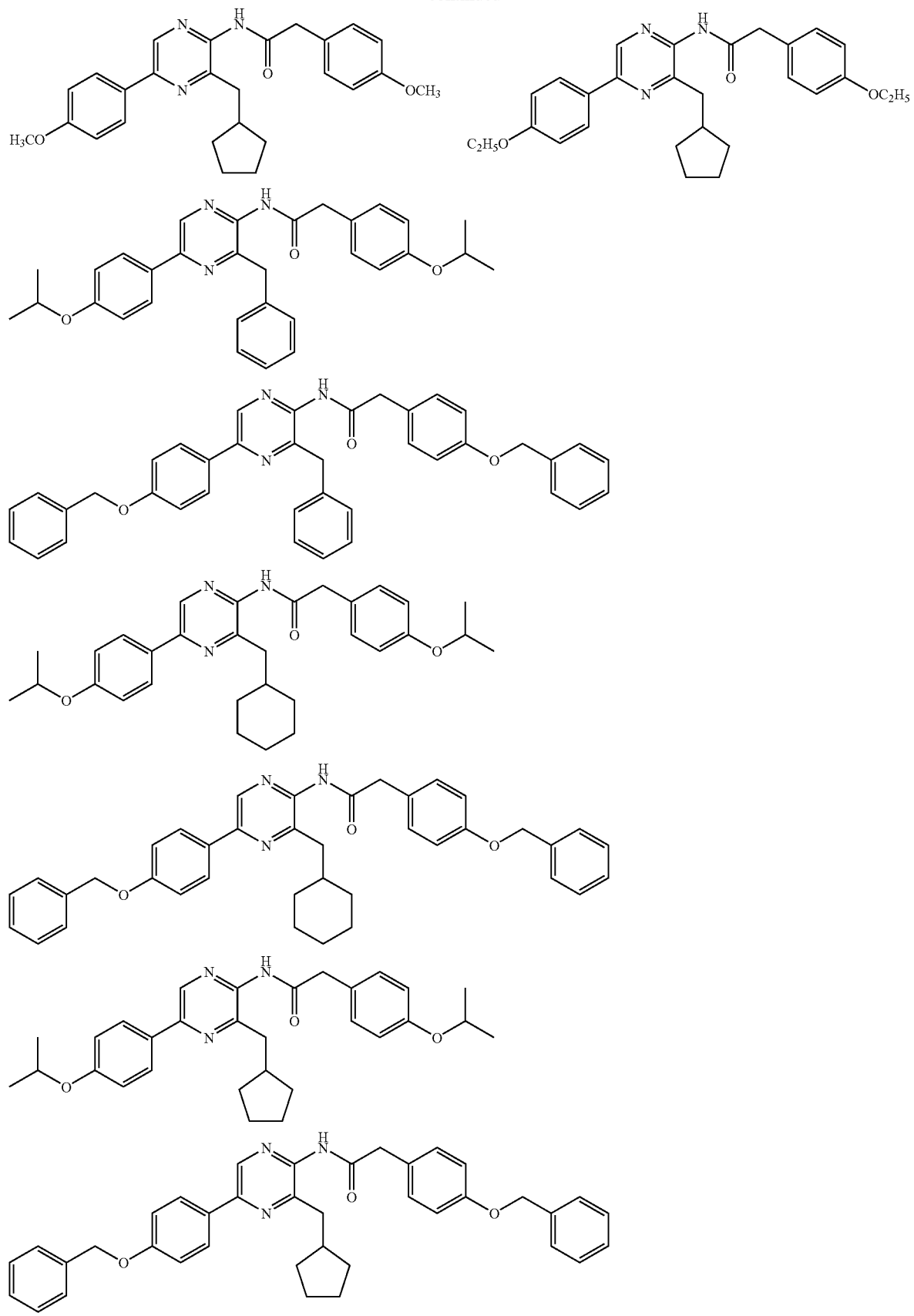

In another embodiment of the present invention, the di-O-methylcoelenteramide analog represented by general formula (3) described above is, for example, a compound selected from the compounds described below.

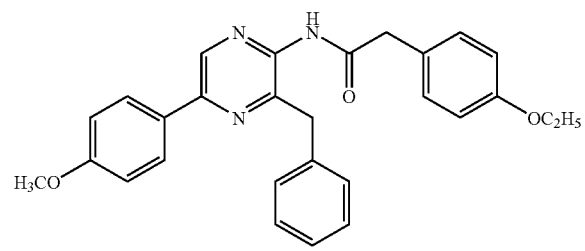
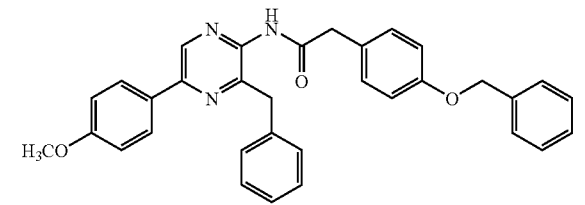
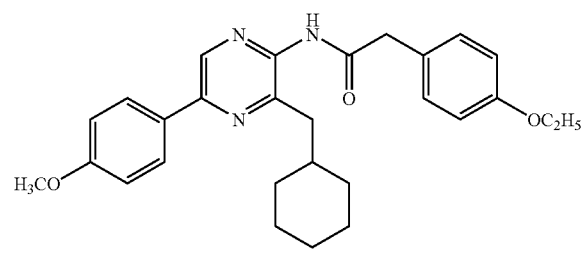
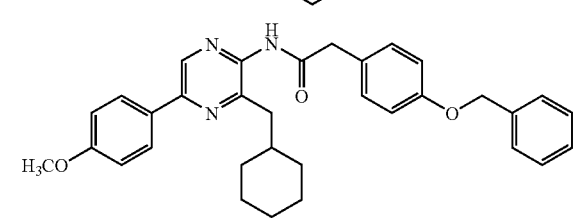
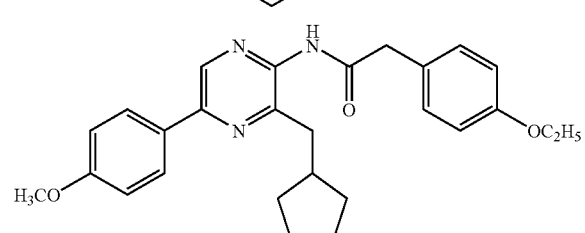
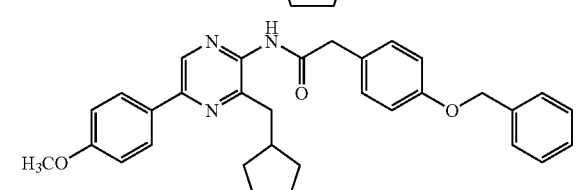
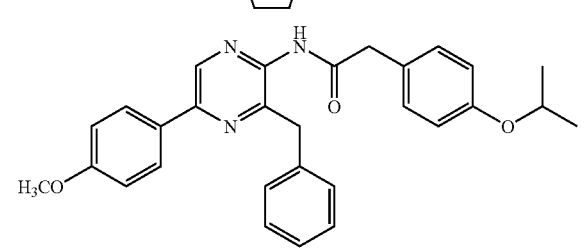

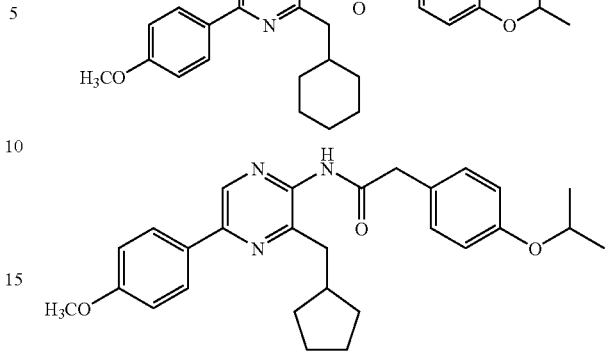

In a still further embodiment of the present invention, the di-O-methylcoelenteramide analog represented by general formula (3) above is, for example, a compound selected from the group consisting of the compounds below.

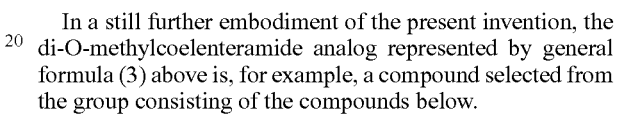
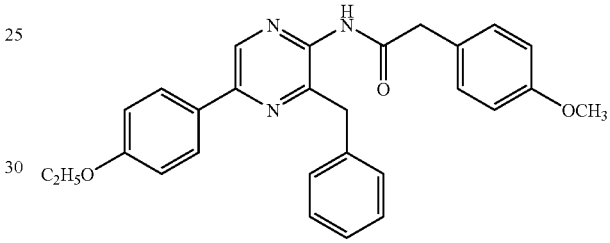
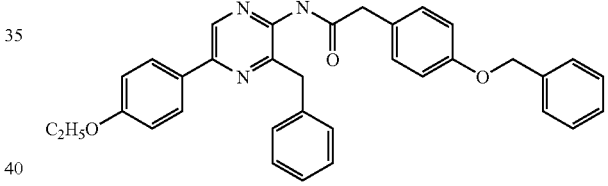
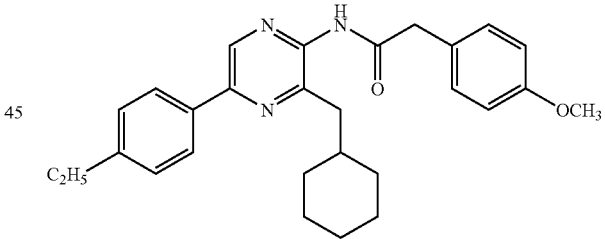
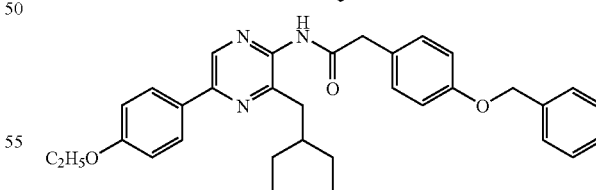
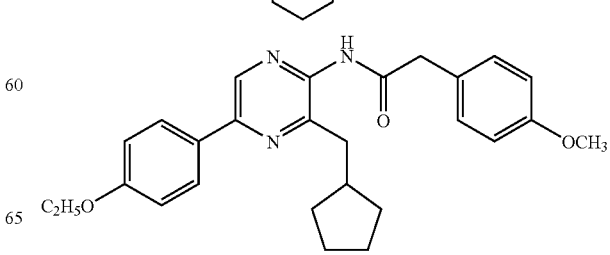

-continued

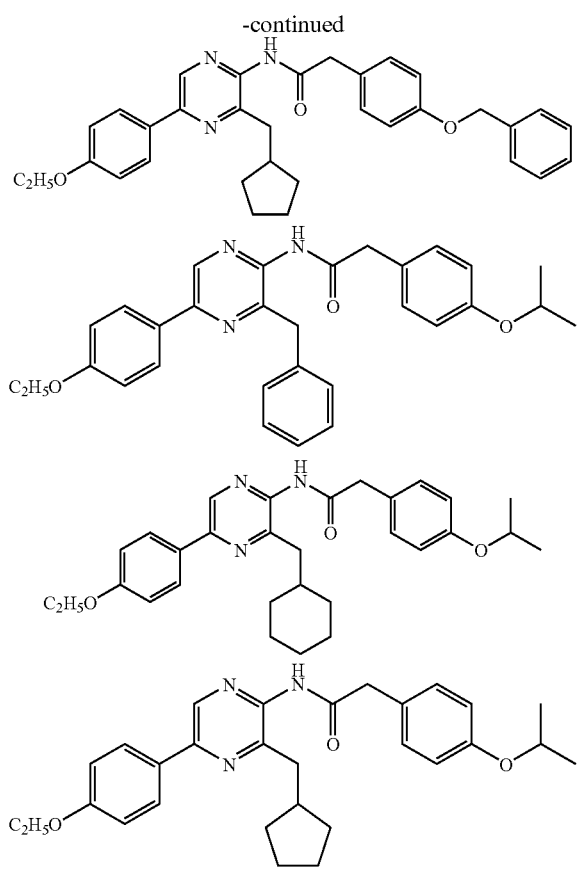

In a still further embodiment of the present invention, the di-O-methylcoelenteramide analog represented by general formula (3) above is, for example, a compound selected from the group consisting of the compounds below.

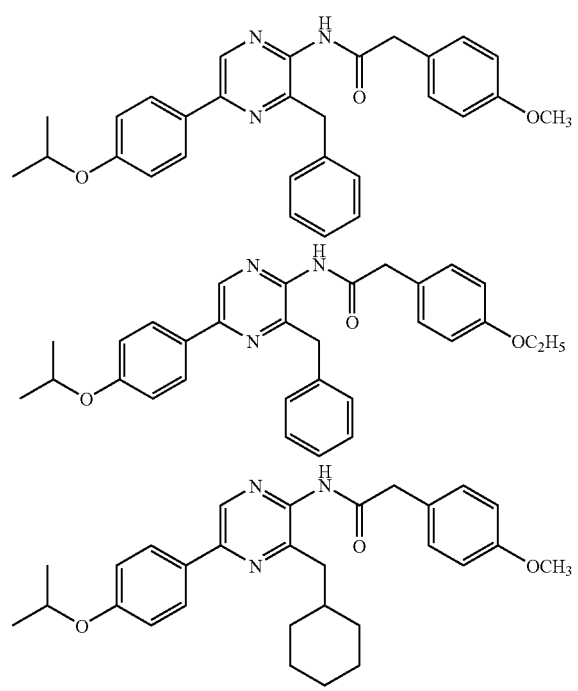

-continued

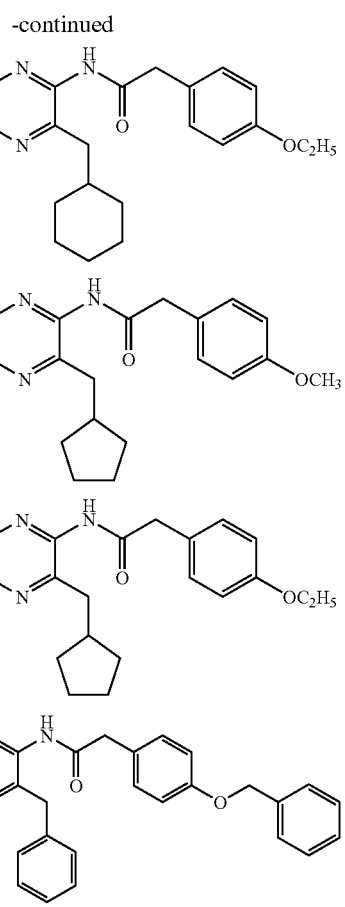

In a still further embodiment of the present invention, the di-O-methylcoelenteramide analog represented by general formula (3) above is, for example, a compound selected from the group consisting of the compounds below.

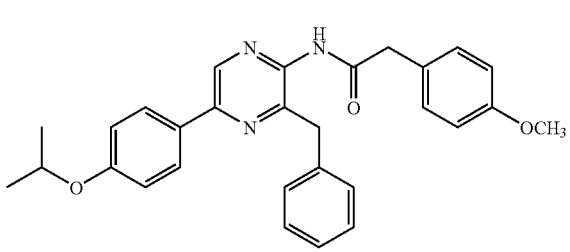

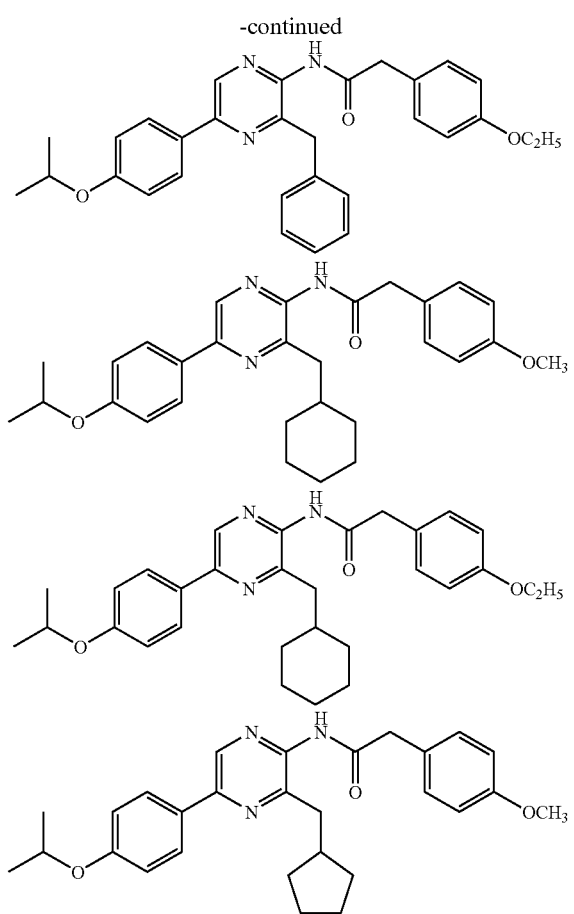
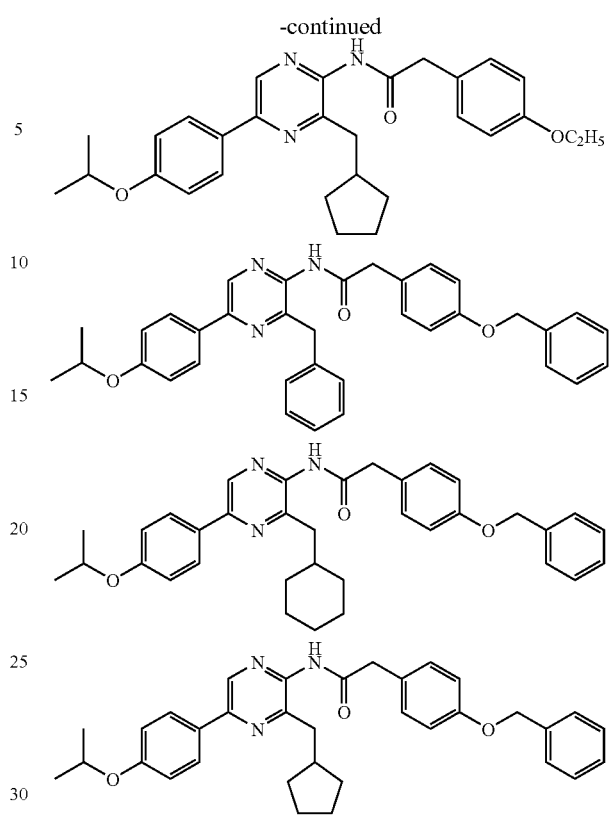
In some embodiments of the present invention, the di-O-methylcoelenteramide or its analog is preferably a compound selected from the group consisting of the compounds below.
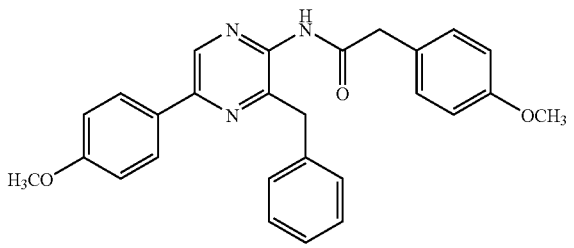
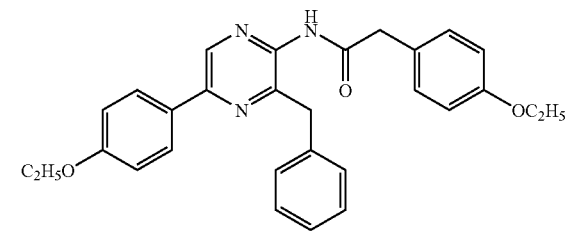
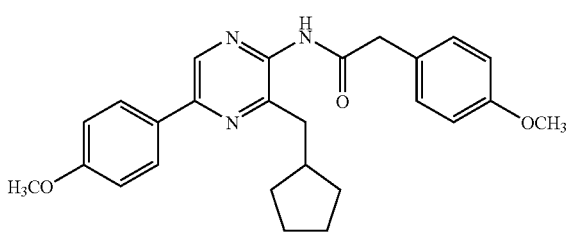
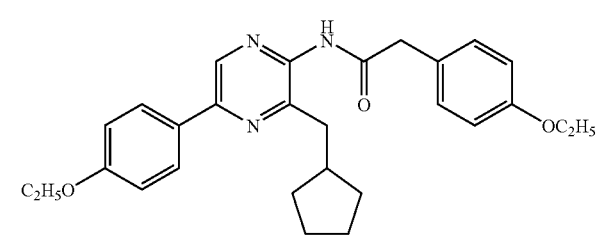
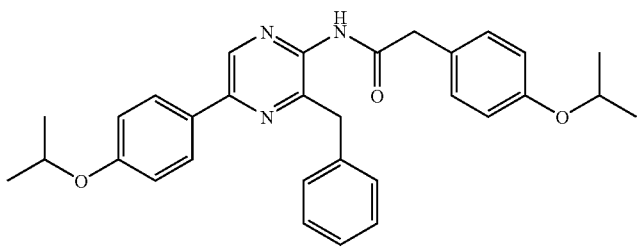

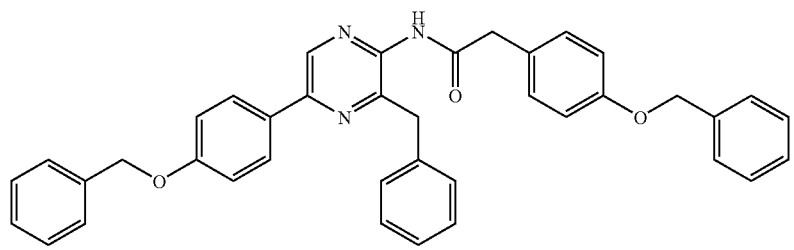
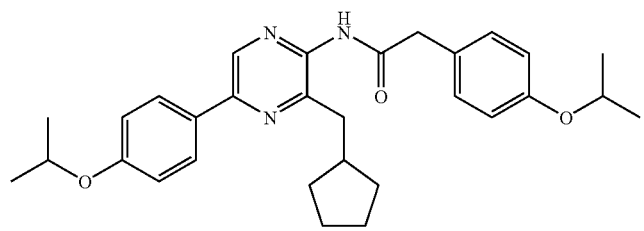
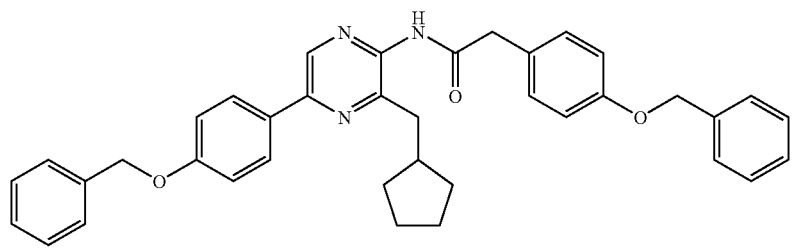
In another embodiment of the present invention, the di-O-methylcoelenteramide analog is preferably a compound selected from the group consisting of the compounds below.
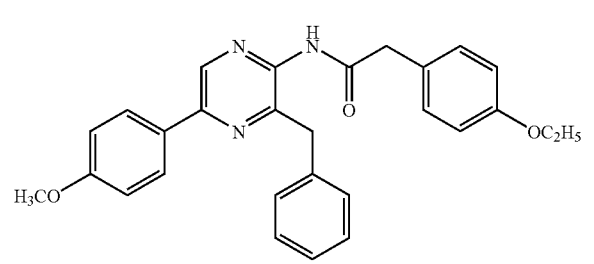
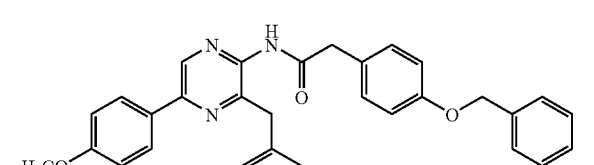
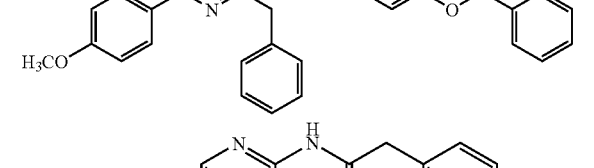
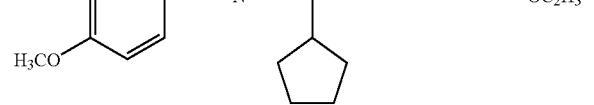
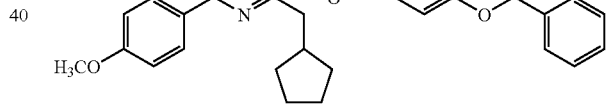
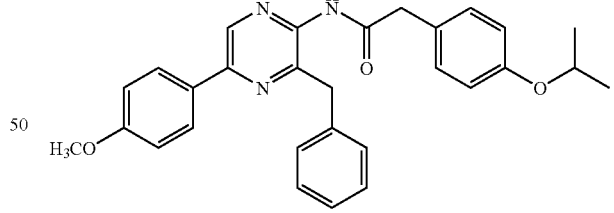
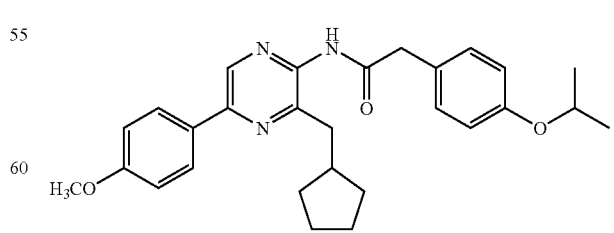
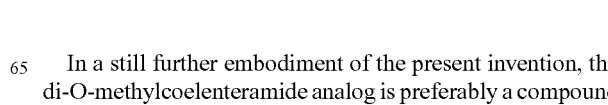
In a still further embodiment of the present invention, the di-O-methylcoelenteramide analog is preferably a compound selected from the group consisting of the compounds below.

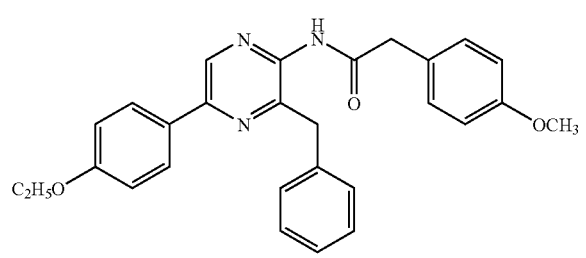
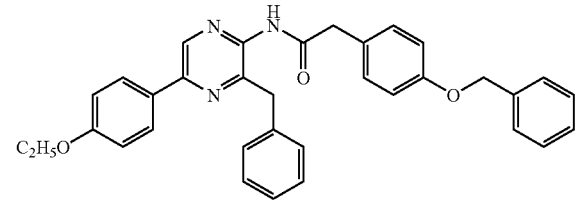
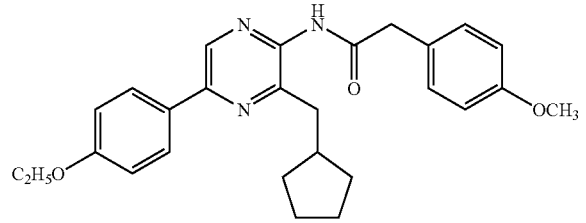
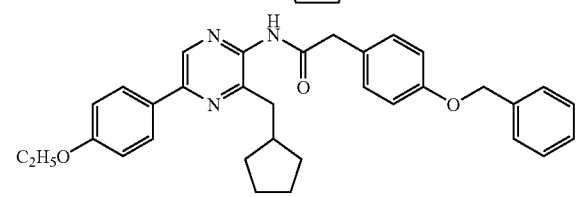
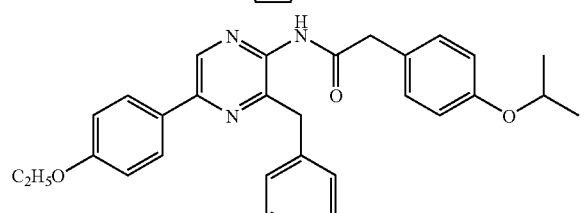
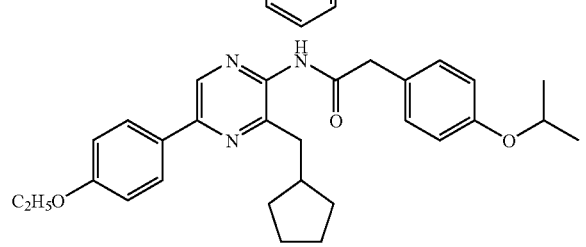
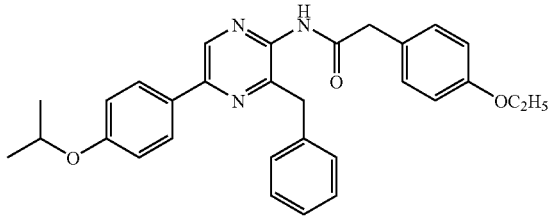
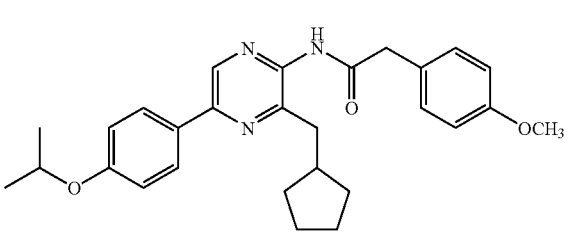
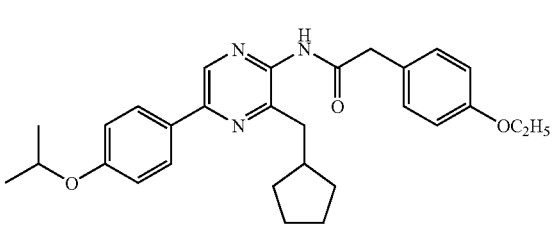
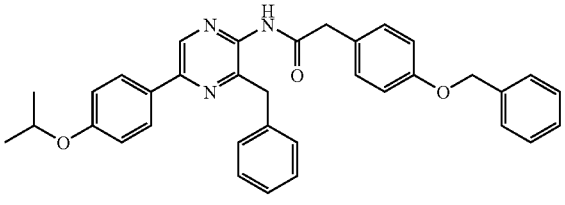
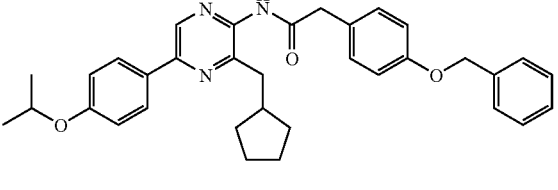
In a still further embodiment of the present invention, the di-O-methylcoelenteramide analog is preferably a compound selected from the group consisting of the compounds below.
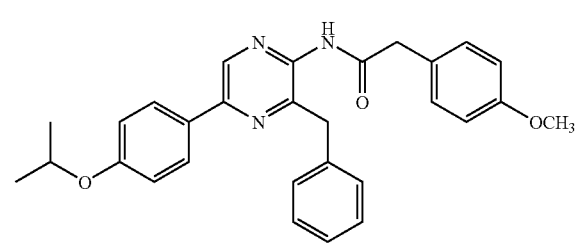
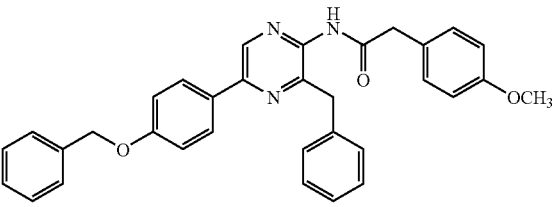
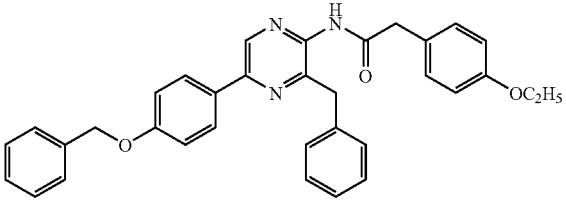
In a still further embodiment of the present invention, the di-O-methylcoelenteramide analog is preferably a compound selected from the group consisting of the compounds below.

-continued

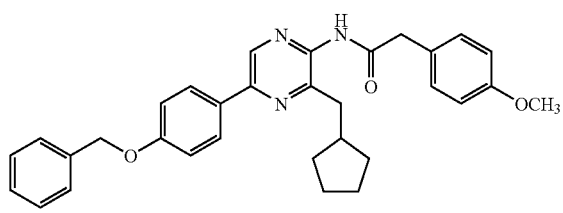

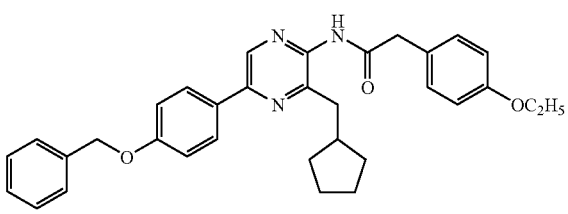

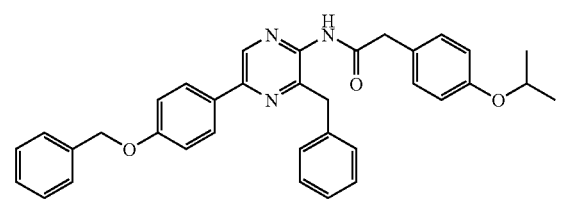

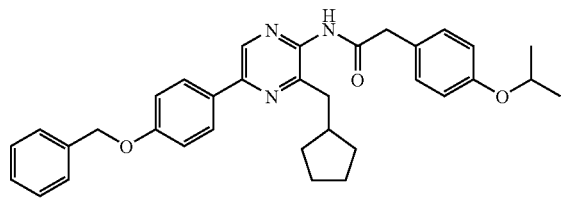

In an embodiment of the present invention, the di-O-methylcoelenteramide or its analog is di-O-methylcoelenteramide below.

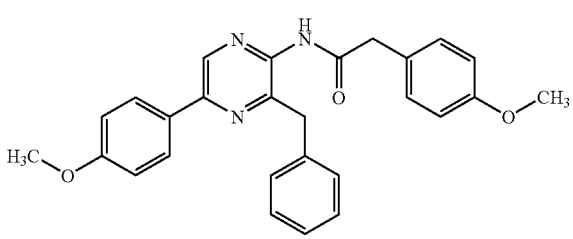

The present invention provides the process for producing the di-O-methylcoelenteramide or its analogs described above. More specifically, the present invention provides the process for producing the di-O-methylcoelenteramide or its analogs (the compounds represented by general formula (3)), which comprises the O-methylcoelenteramine or its analogs (the compounds represented by general formula (1)) with a 4-methoxyphenylacetyl halide or its analogs (the compounds represented by general formula (2)). That is, the present invention provides the process for producing the compound represented by general formula (3) below:

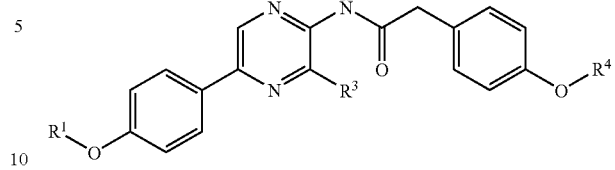

(wherein, $R^1$ represents an alkyl having 1 to 3 carbon atoms or an arylalkyl having 7 to 10 carbon atoms, $R^3$ represents an alkyl having 1 to 7 carbon atoms which may optionally be substituted with an alicyclic group, an alicyclic group or an arylalkyl having 7 to 10 carbon atoms), and, $R^4$ represents an alkyl having 1 to 3 carbon atoms or an arylalkyl having 7 to 10 carbon atoms), which comprises reacting the compound represented by general formula (1) below:

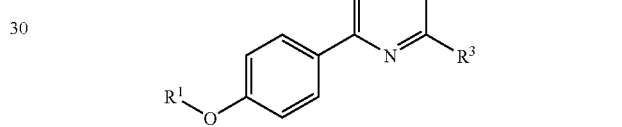

(wherein $R^1$ and $R^3$ have the same significance as defined above, and, $R^2$ is amino), with the compound represented by general formula (2) below:

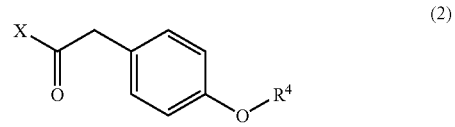

(wherein, X is a splitting-off group and $R^4$ has the same significance as defined above).

In general formula (1) or general formula (2), $R^1$, $R^3$ and $R^4$ have the same significance as defined in general formula (3) above.

In general formula (2), the splitting-off group shown by X includes, for example, a halogen (e.g., chlorine, bromine or iodine), a reactive residue of a sulfonic acid (e.g., methanesulfonyloxy, benzenesulfonyloxy or toluenesulfonyloxy), and an acyloxy for forming an acid anhydride (e.g., (4-$R^{40}$) $C_6H_4CH_2COO$— (wherein $R^4$ has the same significance as defined above)). Among them, a halogen is preferred and chlorine is more preferred.

The O-methylcoelenteramine or its analogs represented by general formula (1) above includes, for example, a compound selected from the compounds below.

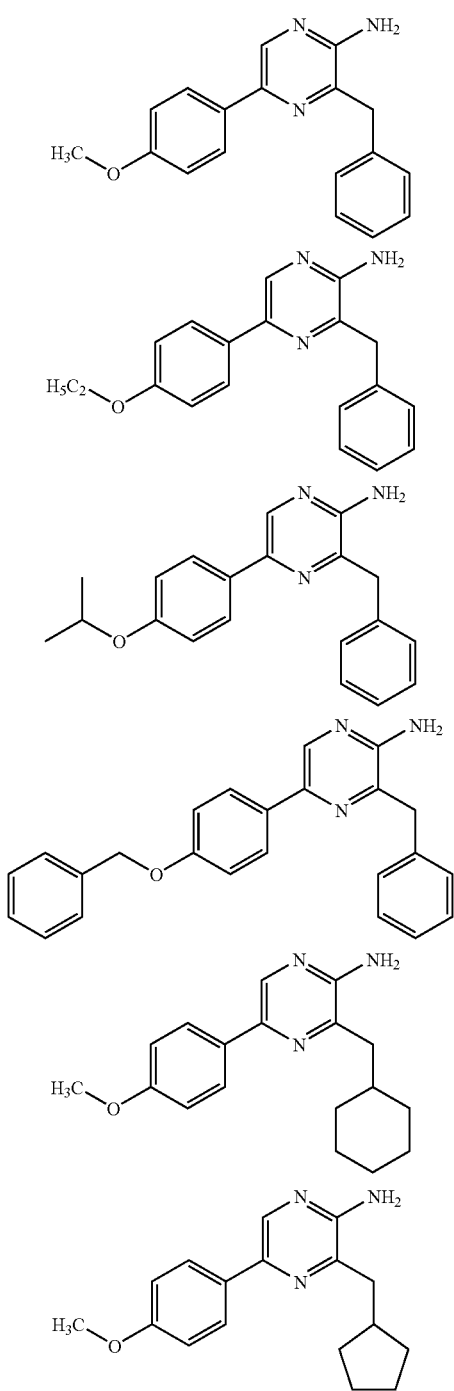

The O-methylcoelenteramine or its analog is preferably a compound selected from the group consisting of the compounds described below.

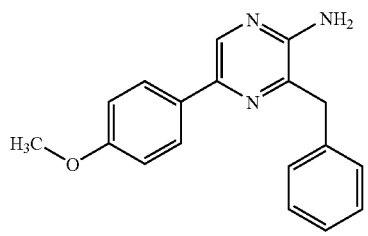

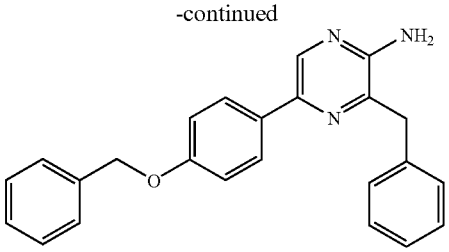

In one embodiment of the present invention, the O-methylcoelenteramine or its analog is the compound described below.

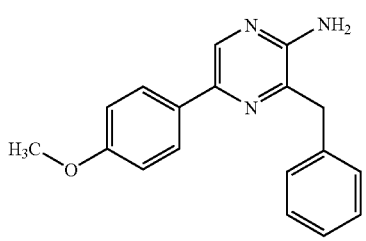

The O-methylcoelenteramine or its analog represented by general formula (1) can be produced by known production processes or is commercially available. For example, the O-methylcoelenteramine or its analog represented by general formula (1) can be produced by processes described in Kishi et al., Tetrahedron Lett., 13, 2747-2748 (1972), or Adamczyk et al., Org. Prep. Proced. Int., 33, 477-485 (2001), or by modifications of these processes.

The 4-methoxyphenylacetyl halide or its analog represented by general formula (2) above includes, for example, a compound selected from the group consisting of the compounds below.

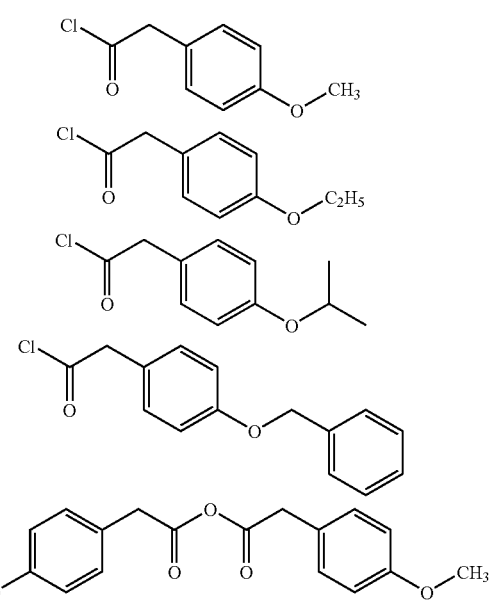

The 4-methoxyphenylacetyl halide or its analog is preferably a compound selected from the group consisting of the compounds below.

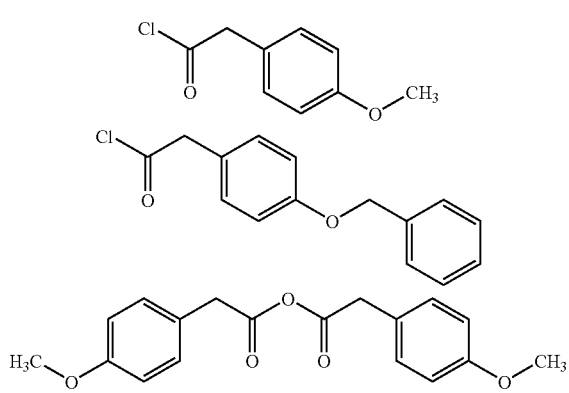

In one embodiment of the present invention, the 4-methoxyphenylacetyl halide or its analog is 4-methoxyphenylacetyl chloride shown below.

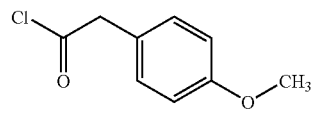

The 4-methoxyphenylacetyl halide or its analog represented by general formula (2) can be prepared by known processes or is commercially available. Specifically, any compound can be produced either by a process which comprises reacting an excess of thionyl chloride with the corresponding carboxylic acid, heating the reaction mixture under reflux and concentrating under reduced pressure, or a process which comprises reacting oxalyl dichloride with the corresponding carboxylic acid in a dichloromethane solvent in the presence of a catalytic amount of N,N-dimethylformamide (DMF) and concentrating under reduced pressure. Also, 4-methoxyphenylacetyl chloride can be purchased from Aldrich Inc., and 4-benzyloxyphenylacetyl chloride and 4-methoxyphenylacetyl anhydride from Tokyo Chemical Industry Co., Ltd.

The di-O-methylcoelenteramide or its analogs represented by general formula (3) can be produced by reacting the O-methylcoelenteramine or its analogs represented by general formula (1) with the 4-methoxyphenylacetyl halide or its analogs represented by general formula (2), e.g., in an organic solvent in the presence of a base or in a basic organic solvent. More specifically, the di-O-methylcoelenteramide can be produced by the processes described in EXAMPLES later given or by their modifications.

Herein, various organic solvents or basic organic solvents can be used for the process of the present invention for producing di-O-methylcoelenteramide or its analogs but an organic solvent or a basic organic solvent other than water-based solvents or alcohols is particularly preferred. Examples of the organic solvent and the basic organic solvent are pyridine, dichloromethane, chloroform, acetonitrile, tetrahydrofuran, ethyl acetate, acetone, toluene, dioxane, ether, etc. These solvent can be used singly or as admixtures thereof.

The base used for the process of the present invention for producing di-O-methylcoelenteramide or its analogs is not particularly limited and various bases can be used. Examples include pyridine, triethylamine, diisopropylethylamine, 4-dimethylaminopyridine, lutidine, colidine, and the like. These bases can be used singly or as admixtures thereof.

In the process of the present invention for producing di-O-methylcoelenteramide or its analogs, the reaction temperature and reaction time are not particularly limited and are, for example, at −20° C. to 200° C. for 1 to 72 hours, preferably at 0° C. to 100° C. for 6 to 36 hours, and more preferably at room temperature to 50° C. for 12 to 24 hours.

In one embodiment, the present invention provides the process for producing di-O-methylcoelenteramide represented by formula below:

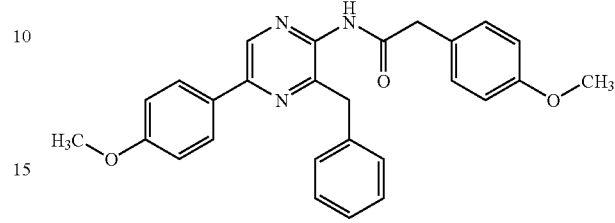

which comprises reacting O-methylcoelenteramine represented by formula below:

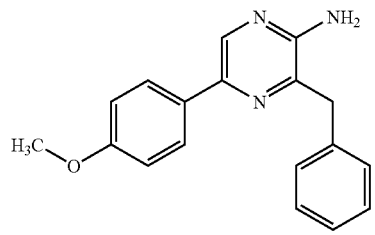

with 4-methoxyphenylacetyl chloride represented by formula below.

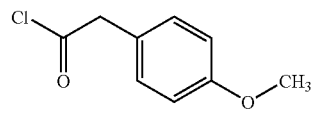

1.2. Production of Coelenteramide or its Analogs

The present invention further provides the process for producing coelenteramide or its analogs (the compounds represented by general formula (4)) which comprises splitting off the group shown by $R^1$ and the group shown by $R^4$ from di-O-methylcoelenteramide or its analogs (the compounds represented by general formula (3)). That is, the present invention provides the process for producing the compound represented by formula below:

(4)

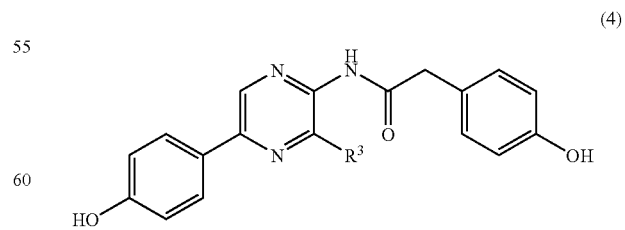

(wherein $R^3$ represents an alkyl having 1 to 7 carbon atoms which may optionally be substituted with an alicyclic group, an alicyclic group or an arylalkyl having 7 to 10 carbon atoms), which comprises splitting-off the group shown by $R^1$ and the group shown by $R^4$ from the compounds represented by general formula (3):

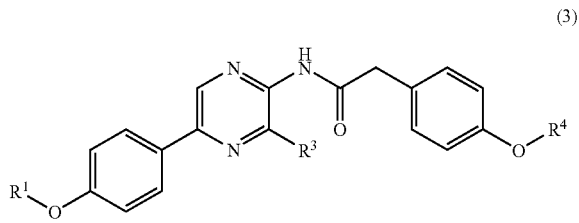

(3)

(wherein,
$R^1$ represents an alkyl having 1 to 3 carbon atoms or an arylalkyl having 7 to 10 carbon atoms,
$R^3$ has the same significance as defined above, and,
$R^4$ represents an alkyl having 1 to 3 carbon atoms or an arylalkyl having 7 to 10 carbon atoms).

In the process of the present invention for producing coelenteramide or its analogs, the di-O-methylcoelenteramide or its analogs represented by general formula (3) are as defined above. Examples of the di-O-methylcoelenteramide or its analogs include compounds produced by the process of the present invention for producing coelenteramide or its analogs described above.

In the process of the present invention for producing coelenteramide or its analogs, the group shown by $R^1$ and the group shown by $R^4$ can be split off in a conventional manner and its splitting-off procedures are not particularly limited. For example, methyl can be removed by the procedures described in EXAMPLES or modifications thereof.

Herein, various solvents can be used as the solvent for the process of the present invention for producing coelenteramide or its analogs, and are preferably non-polar solvents. Examples of the solvent include dichloromethane, chloroform, tetrahydrofuran, toluene, dioxane, ether, and the like. These solvents can be used singly or as admixtures thereof.

In the process of the present invention for producing coelenteramide or its analogs, the reaction temperature and reaction time are not particularly limited and are, for example, at $-100°$ C. to $200°$ C. for 1 to 72 hours, preferably at $-20°$ C. to $100°$ C. for 6 to 36 hours, and more preferably at $0°$ C. to $50°$ C. for 12 to 24 hours.

Examples of the coelenteramide or its analogs represented by general formula (4), which are produced by the process of the present invention, include a compound selected from the group consisting of the compounds below.

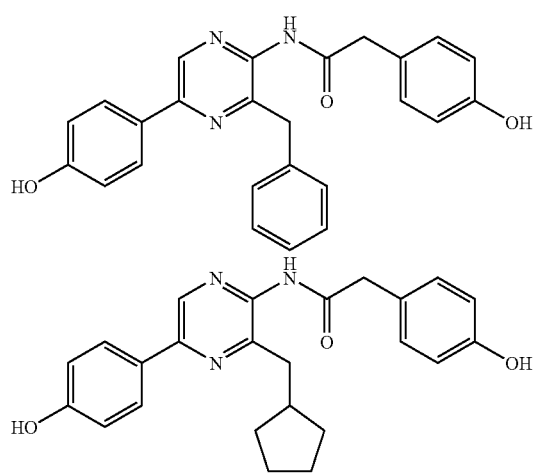

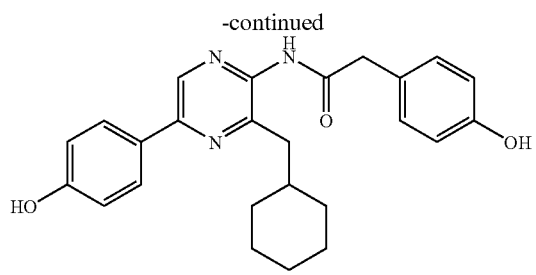

The coelenteramide or its analogs are preferably a compound selected from the group consisting of the compounds below.

In one embodiment of the present invention, the coelenteramide or its analog is coelenteramide shown below.

In one embodiment, the present invention provides the process for producing coelenteramide shown by:

which comprises demethylation of di-O-methylcoelenteramide shown by:

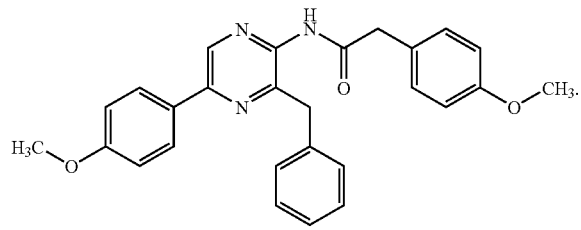

2. Fluorescent Protein

As illustrated in FIG. 6, a green fluorescent protein (gFP) can be produced by reacting or mixing (or combining) coelenteramide or its analogs (compounds represented by general formula (4)) with an apoprotein such as apoaequorin, etc., in the presence of a chelating agent such as EDTA, etc., for sequestering or removing a calcium or a divalent or trivalent ion substitutable for the calcium ion. A blue fluorescent protein (BFP) can be produced by adding calcium ions to gFP.

As further illustrated in FIG. 6, BFP can also be produced by reacting coelenteramide or its analogs with an apoprotein such as apoaequorin, etc., in the presence of a calcium ion or a divalent or trivalent ion substitutable for the calcium ion. The calcium-binding photoprotein such as aequorin, etc. may also be produced by reacting coelenterazine or its analogs with gFP in the presence of a chelating agent for sequestering a calcium ion or a divalent or trivalent ion substitutable for the calcium ion.

2.1. Green Fluorescent Protein (gFP)

2.1.1. Process for Producing Green Fluorescent Protein (gFP)

In the process of the present invention for producing the green fluorescent protein (gFP), the green fluorescent protein (gFP) produced is a complex of a apoprotein and coelenteramide or its analog which is coordinated with the apoprotein of the photoprotein. gFP can emit fluorescence under the excitation of light.

According to the present invention, gFP is produced as follows from coelenteramide or its analogs. More specifically, gFP is produced by reacting coelenteramide or its analogs (e.g., the compounds represented by general formula (4)) with the apoprotein of a calcium-binding photoprotein, in the presence of a chelating agent for sequestering a calcium ion or a divalent or trivalent ion substitutable for calcium ion.

In the present invention, coelenteramide or its analogs used to produce gFP includes, for example, the compounds represented by general formula (4) described above. The compounds represented by general formula (4) are described above. Examples of coelenteramide or its analog include the compounds produced by the process of the present invention for producing coelenteramide or its analogs described above.

In the present invention, the chelating agent used to produce gFP can be any compound and is not particularly limited, so long as it strongly binds to calcium ions or divalent or trivalent ions substitutable for the calcium ions. Examples of the chelating agent include ethylenediaminetetraacetic acid (EDTA), ethylene glycol-bis(β-aminoethyl ether)-N,N,N',N'-tetraacetic acid (EGTA), trans-1,2-diaminocyclohexane-N,N,N',N'-tetraacetic acid (CyDTA), N-(2-hydroxyethyl)iminodiacetic acid (HIDA) and the like. As used herein, the divalent or trivalent ion substitutable for the calcium ion refers to a divalent or trivalent ion that causes a luminescence reaction upon reaction with the calcium-binding photoprotein in place of calcium ions. In other words, the divalent or trivalent ion has the action equivalent to the calcium ion on the calcium-binding photoprotein. Examples of the calcium ion or the divalent or trivalent ion substitutable for the calcium ion include calcium ion ($Ca^{2+}$), magnesium ion ($Mg^{2+}$), strontium ion ($Sr^{2+}$), barium ion ($Ba^{2+}$), lead ion ($Pb^{2+}$), cobalt ion ($Co^{2+}$), nickel ion ($Ni^{2+}$), cadmium ion ($Cd^{2+}$), yttrium ion ($V^{+}$), lanthanum ion ($La^{3+}$), samarium ion ($Sm^{3+}$), europium ion ($Eu^{3+}$), dysprosium ion ($Dy^{3+}$), thulium ion ($Tm^{3+}$), ytterbium ion ($Yb^{3+}$), and the like. Among them, the divalent metal ions are preferred, more preferably the divalent metal ions other than transition metals, e.g., $Ca^{2+}$, $Sr^{2+}$, $Pb^{2+}$, etc.

The amount of the chelating agent used to produce gFP is not particularly limited unless its concentration affects regeneration of gFP. Since it is demonstrated that 3 mol of calcium ions bind to 1 mol of ion apoaequorin, at least 3 mol is preferred.

Examples of the apoprotein in the calcium-binding photoprotein used to produce gFP according to the present invention include apoaequorin, apoclytin-I, apoclytin-II, apoobelin, apomitrocomin, apomineopsin, apobervoin, and the like. In an embodiment of the present invention, the apoprotein is apoaequorin, apoclytin-I, apoclytin-II, apoobelin, apomitrocomin, etc., for example, apoaequorin. These apoproteins may be obtained from natural sources or genetically engineered. Furthermore, the amino acid sequence may be mutated from the natural sequence by gene recombination technology, as long as the apoproteins are capable of forming gFP.

The nucleotide sequences and amino acid sequences of the apoproteins of photoproteins obtained from the nature (natural apoproteins) are as follows. The nucleotide sequence and amino acid sequence of natural apoaequorin are shown by SEQ ID NO: 1 and SEQ ID NO: 2, respectively. The nucleotide sequence and amino acid sequence of natural apoclytin-I are represented by SEQ ID NO: 3 and SEQ ID NO: 4. The nucleotide sequence and amino acid sequence of natural apoclytin-II are represented by SEQ ID NO: 5 and SEQ ID NO: 6. The nucleotide sequence and amino acid sequence of natural apomitrocomin are represented by SEQ ID NO: 7 and SEQ ID NO: 8. The nucleotide sequence and amino acid sequence of natural apoobelin are represented by SEQ ID NO: 9 and SEQ ID NO: 10. The nucleotide sequence and amino acid sequence of natural apobervoin are represented by SEQ ID NO: 11 and SEQ ID NO: 12.

The apoprotein mutated by recombinant technology is a protein selected from the group consisting of (a) to (c) below:

(a) a protein comprising the amino acid sequence of natural apoprotein in which 1 or more amino acids are deleted, substituted, inserted and/or added, and having the activity or function of the apoprotein of a calcium-binding photoprotein;

(b) a protein comprising an amino acid sequence which is at least 90% homologous to the amino acid sequence of natural apoprotein, and having the activity or function of the apoprotein of a calcium-binding photoprotein; and, (c) a protein comprising an amino acid sequence encoded by a polynucleotide that hybridizes under stringent conditions to a polynucleotide comprising a nucleotide sequence complementary to the nucleotide sequence of natural apoprotein, and having the activity or function of the apoprotein of a calcium-binding photoprotein.

Examples of the "natural apoprotein" described above are apoaequorin, apoclytin-I, apoclytin-II, apoobelin, apomitrocomin, apomineopsin, apobervoin, etc. In an embodiment of the present invention, the apoprotein is apoaequorin, apoclytin-I, apoclytin-II, apoobelin, apomitrocomin, etc., preferably apoaequorin. The amino acid sequences and nucleotide sequences of these natural apoproteins are as described above.

The "activity or function of the apoprotein in a calcium-binding photoprotein" means the activity or function of the apoprotein which binds to the peroxide of coelenterazine or the peroxide of a coelenterazine analog to produce the calcium-binding photoprotein. Specifically, "the protein binds to the peroxide of coelenterazine or the peroxide of a coelenterazine analog to produce the calcium-binding photoprotein" not only means that (1) the protein binds to the peroxide of coelenterazine or the peroxide of a coelenterazine analog to produce the calcium-binding photoprotein, but also means that (2) the protein is brought in contact with coelenterazine or its derivative in the presence of oxygen to produce a photoprotein (complex) containing the protein and the peroxide of coelenterazine or the peroxide of a coelenterazine analog. As used herein, the term "contact" means that the protein and coelenterazine or its analog are allowed to be present in the same reaction system, and includes, for example, the protein being added to a container charged with coelenterazine or its analog, coelenterazine or its analog being added to a container charged with the protein, the protein being mixed with coelenterazine or its analog, and the like. The "coelenterazine analog" refers to a compound capable of constituting as the apoprotein a calcium-binding photoprotein such as aequorin, etc. as in coelenterazine. Examples of coelenterazine or its analog include coelenterazine, h-coelenterazine, f-coelenterazine, cl-coelenterazine, n-coelenterazine, cp-coelenterazine, ch-coelenterazine, hch-coelenterazine, fch-coelenterazine, e-coelenterazine, ef-coelenterazine, ech-coelenterazine, hcp-coelenterazine, and the like. It is later described how these coelenterazines and analogs thereof are made available.

The range of "1 or more" in "the amino acid sequence in which 1 or more amino acids are deleted, substituted, inserted and/or added" is, for example, 1 to 20, 1 to 15, 1 to 10, 1 to 9, 1 to 8, 1 to 7, 1 to 6 (1 to several), 1 to 5, 1 to 4, 1 to 3, 1 to 2, and 1. In general, the less the number of amino acids deleted, substituted, inserted or added, the more preferable. In the deletion, substitution, insertion and addition of the amino acid residues described above, two or more may occur concurrently. Such domains can be acquired site-directed mutagenesis described in Sambrook J. et al., Molecular Cloning: A Laboratory Manual, Third Edition, Cold Spring Harbor Laboratory Press (2001); Ausbel F. M. et al., Current Protocols in Molecular Biology, Supplement 1-38, John Wiley and Sons (1987-1997); Nuc. Acids. Res., 10, 6487 (1982); Proc. Natl. Acad. Sci. USA, 79, 6409 (1982); Gene, 34, 315 (1985); Nuc. Acids. Res., 13, 4431 (1985); Proc. Natl. Acad. Sci. USA, 82, 488 (1985); etc.

The range of "90% or more" in the "amino acid sequence which is 90% or more homologous" is, for example, 90% or more, 91% or more, 92% or more, 93% or more, 94% or more, 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, or 99.9% or more. It is generally preferable for the numerical value indicating the degree of homology to be higher. The homology between amino acid sequences or nucleotide sequences can be determined using a sequencing program such as BLAST (see, e.g., Altzchul, S. F. et al., J. Mol. Biol., 215, 403 (1990), etc.) or the like. When BLAST is used, the default parameters for the respective programs are employed.

The "polynucleotide that hybridizes under stringent conditions" refers to a polynucleotide (e.g., DNA) which is obtained by, for example, colony hybridization, plaque hybridization or Southern hybridization using as the probe all or part of the polynucleotide comprising a nucleotide sequence complementary to the nucleotide sequence of natural apoprotein. Specific examples include a polynucleotide which can be identified by performing hybridization at 65° C. in the presence of 0.7 to 1.0 mol/L NaCl using a filter on which the polynucleotide from a colony or plaque is immobilized, then washing the filter at 65° C. with an SSC (saline-sodium citrate) solution having a concentration of 0.1 times to 2 times (a 1×SSC solution is composed of 150 mmol/L of sodium chloride and 15 mmol/L of sodium citrate).

Hybridization may be performed in accordance with methods described in textbooks, e.g., Sambrook, J. et al.: Molecular Cloning: A Laboratory Manual, Third Edition, Cold Spring Harbor Laboratory Press (2001), Ausbel F. M. et al., Current Protocols in Molecular Biology, Supplement 1-38, John Wiley and Sons (1987-1997), Glover D. M. and Hames B. D., DNA Cloning 1: Core Techniques, A practical Approach, Second Edition, Oxford University Press (1995), etc., or their modifications.

As used herein, "stringent conditions" may refer to less stringent conditions, moderately stringent conditions and highly stringent conditions. The "less stringent conditions" are, for example, the conditions under 5×SSC, 5×Denhardt's solution, 0.5% (w/v) SDS and 50% (v/v) formamide at 32° C. The "moderately stringent conditions" are, for example, the conditions under 5×SSC, 5×Denhardt's solution, 0.5% (w/v) SDS and 50% (v/v) formamide at 42° C. The "highly stringent conditions" are, for example, the conditions under 5×SSC, 5×Denhardt's solution, 0.5% (w/v) SDS and 50% (v/v) formamide at 50° C. The more stringent the conditions are, the higher the complementarity required for double strand formation. Specifically, for example, under these conditions, a polynucleotide (e.g., DNA) of higher homology is expected to be obtained efficiently at higher temperatures, although multiple factors are involved in hybridization stringency, including temperature, probe concentration, probe length, ionic strength, time and base concentration; one skilled in the art may appropriately select these factors to realize a similar stringency.

When a kit commercially available is used for the hybridization, for example, AlkPhos Direct Labeling Reagents (manufactured by Amersham Pharmacia) can be used. According to the protocol attached to the kit in this case, incubation with a labeled probe is performed overnight, the membrane is then washed with a primary wash buffer containing 0.1% (w/v) SDS at 55° C., and finally the hybridized DNA can be detected.

Other hybridizable polynucleotides include, as calculated by a sequencing program such as BLAST or the like using the default parameters, DNAs having at least 60%, at least 65%, at least 70%, at least 75%, at least 80%, at least 85%, at least 88%, at least 90%, at least 92%, at least 95%, at least 97%, at least 98%, at least 99%, at least 99.3%, at least 99.5%, at least 99.7%, at least 99.8%, or at least 99.9% homology to the polynucleotide encoding the amino acid sequence of the apoprotein. The homology of an amino acid sequence or a nucleotide sequence can be determined using the method described above.

In some embodiments of the present invention, serine residues are substituted for all cysteine residues in the apoprotein. When free SH groups of the cysteine residues in the apoprotein are oxidized to form S—S bonds, gFP loses its chemiluminescent activity. Accordingly, the apoprotein in which the cysteine residues are substituted with serine residues to disable the ability to form S—S bonds does not lose a great deal of the chemiluminescent activity but continues to keep the activity because of the failure to form S—S bonds.

The amount of the coelenteramide or its analog used to produce gFP is not particularly limited and is in a range of, e.g., 1 mol to 5 mol, preferably 1 mol to 2 mol, more preferably 1 mol to 1.2 mol.

In the production of gFP, it is preferred to perform the reaction of coelenteramide or its analog with apoprotein in the presence of a reducing agent. Examples of the reducing agent used herein include dithiothreitol (DTT), mercaptoethanol, etc. The amount of the reducing agent used to produce gFP is not particularly limited so long as the amount does not affect the regeneration of gFP but the concentration is preferably sufficient to prevent the formation of S—S bonds by the presence of cysteine residues at the three positions of apoaequorin. Such a concentration is, for example, 1 mM dithiothreitol or 0.1% mercaptoethanol in a final concentration.

In the process for producing gFP, the reaction temperature and reaction time are not particularly limited and are, for example, at 0° C. to 42° C. for 0.1 to 2 hours, at 4° C. to 37° C. for 0.1 to 2 hours, or at 4° C. to 15° C. for 0.1 to 24 hours.

The produced gFP may be further purified. Purification of gFP can be performed in a conventional manner of separation/purification. The separation/purification includes, for example, precipitation with ammonium sulfate, gel filtration chromatography, ion exchange chromatography, affinity chromatography, reversed phase high performance liquid chromatography, dialysis, ultrafiltration, etc., alone or in appropriate combination.

In some embodiments, the present invention provides a process for producing a green fluorescent protein (gFP), which comprises reacting the compound shown by formula below:

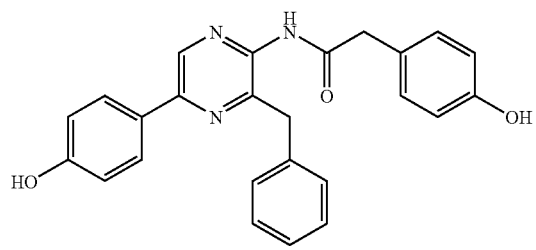

with apoaequorin in the presence of the chelating agent for sequestering a calcium ion or a divalent or trivalent ion substitutable for the calcium ion. In one embodiment of the present invention, gFP is produced by reacting coelenteramide with apoaequorin in the presence of EDTA, as shown in FIG. 5.

2.1.2. Application of Green Fluorescent Protein (gFP)

(1) Use as a Reporter Protein gFP can be used as a reporter protein to determine the transcription activity of a promoter, etc. For instance, a polynucleotide encoding apoprotein is fused to a target promoter or other expression control sequence (e.g., an enhancer, etc.) to construct a vector. The vector is transfected to a host cell, and then coelenteramide or its analog is brought in contact with the host cell in the presence of the chelating agent for sequestering a calcium ion or a divalent or trivalent ion substitutable for the calcium ion to produce gFP. By detecting the fluorescence from gFP, the activity of the target promoter or other expression control sequence can be determined.

(2) Use as a Detection Marker gFP can be used as a detection marker with its fluorescence. The detection marker can be used to detect a target substance in, e.g., immunoassay, hybridization assay, etc. gFP can be used in the form bound to a target substance (protein, nucleic acid, etc.) in a conventional manner including chemical modification. Detection using such detection markers can be carried out in a conventional manner. The detection marker of the invention may also be used to determine distribution of a target substance, for example, by expressing the marker as a fused protein of apoprotein with the target substance, then inserting the fused protein into a cell by a technique such as microinjection, and bringing the protein in contact with coelenteramide or its analog in the presence of the chelating agent for sequestering a calcium ion or a divalent or trivalent ion substitutable for the calcium ion thereby to form gFP. Measurement of the distribution of such a target substance may also be performed by using a detection method such as luminescent imaging. Aside from the transfection to a cell by a technique such as microinjection, the apoprotein may also be used after expression in a cell.

(3) Material for Amusement Supplies gFP can be preferably used as a fluorescence material for amusement supplies. Examples of such amusement supplies are fluorescent soap bubbles, fluorescent ice bars, fluorescent candies, fluorescent color paints, etc. These amusement supplies can be prepared in a conventional manner.

2.2. Blue Fluorescent Protein (BFP)

2.2.1. Process for Producing Blue Fluorescent Protein (BFP)

A blue fluorescent protein (BFP) can be produced by adding calcium ions or divalent or trivalent ions substitutable for the calcium ions to gFP produced by the production process of the invention described above. Alternatively, a blue fluorescent protein (BFP) can also be produced by reacting the coelenteramide or its analog (the compound represented by general formula (4)) produced by the above process of the invention in the presence of calcium ions or divalent or trivalent ions substitutable for the calcium ions with a calcium-binding apoprotein. The blue fluorescent protein (BFP) produced according to the present invention is a complex of a calcium-binding photoprotein and coelenteramide or its analog which is coordinated to the apoprotein of the photoprotein. BFP can emit fluorescence upon excitation of light and can further emit light by a reaction with calcium ions or divalent or trivalent ions substitutable for the calcium ions.

The term "calcium ion or divalent or trivalent ion substitutable for the calcium ion" is the same as defined above. The amount of the calcium ion or the divalent or trivalent ion substitutable for the calcium ion used to produce BFP is not particularly limited; the amount of the calcium ion or the divalent or trivalent ion substitutable for the calcium ion used to produce BFP is not particularly limited, so long as its concentration does not affect regeneration of BFP. Since it is demonstrated that 3 mol of calcium ions bind to 1 mol of ion apoaequorin, at least 3 mol is preferred.

In the production of BFP, the reaction of coelenteramide or its analog with apoprotein is carried out preferably in the presence of a reducing agent. Examples of the reducing agent as used herein include dithiothreitol (DTT), mercaptoethanol, etc.

The amount of the reducing agent used to produce BFP is not particularly limited so long as the amount does not affect the regeneration of BFP but the concentration is preferably sufficient to prevent the formation of S—S bonds by the presence of cysteine residues at the three positions of apoaequorin. Such a concentration is, for example, 1 mM dithiothreitol or 0.1% mercaptoethanol in a final concentration.

In the process of the present invention for producing BFP, the reaction temperature and reaction time are not particularly limited and are, for example, at 0° C. to 42° C. for 0.1 to 2 hours, at 4° C. to 37° C. for 0.1 to 2 hours, or at 4° C. to 15° C. for 0.1 to 24 hours.

The produced BFP may be further purified. Purification of gFP can be performed in a conventional manner of separation/purification. The separation/purification includes, for example, precipitation with ammonium sulfate, gel filtration chromatography, ion exchange chromatography, affinity chromatography, reversed phase high performance liquid chromatography, dialysis, ultrafiltration, etc., alone or in appropriate combination.

2.2.2. Application of Blue Fluorescent Protein (BFP)

(1) Use as a Luminescent Catalyst

BFP of the present invention acts with a luminescence substrate to emit light and can be used as a luminescent catalyst. Thus, the present invention provides a light-emitting method, which comprises bringing coelenterazine or its analog in contact with BFP. As used herein, the term "contact" means that BFP and coelenterazine or its analog are allowed to be present in the same reaction system and includes, for example, BFP being added to a container charged with coelenterazine or its analog, coelenterazine or its analog being added to a container charged with BFP, BFP being mixed with coelenterazine or its analog, and the like.

The luminescence substrate used for the light-emitting method of the present invention includes, for example, coelenterazine or its analog. The "coelenterazine analog" refers to a compound capable of constituting with the apoprotein a calcium-binding photoprotein such as aequorin, etc. as in coelenterazine. Examples of coelenterazine or its analog used as the luminescence substrate include coelenterazine, h-coelenterazine, f-coelenterazine, cl-coelenterazine, n-coelenterazine, cp-coelenterazine, ch-coelenterazine, hch-coelenterazine, fch-coelenterazine, e-coelenterazine, ef-coelenterazine, ech-coelenterazine, hcp-coelenterazine, and the like, preferably coelenterazine, h-coelenterazine and e-coelenterazine. These coelenterazines and analogs thereof can be produced by processes described in, e.g., Shimomura et al. (1988) *Biochem. J.* 251, 405-410, Shimomura et al. (1989) Biochem. J. 261, 913-920, or Shimomura et al. (1990) *Biochem. J.* 270, 309-312, or modifications thereof. Alternatively, they are commercially available from Chisso Corp., Wako Pure Chemicals, Promega Inc., etc. and these commercial products may also be used for the light-emitting method of the present invention.

When these coelenterazines and their analogs are brought in contact with BFP, light is emitted upon oxidation of coelenterazines or their analogs into the corresponding coelenteramides or their analogs by the catalytic reaction of the contacted BFP (whereby carbon dioxide is released). Emission time is generally 0.5 to 3 hours. However, the emission time can be more prolonged or the emission time can be further shortened, depending upon conditions chosen.

(2) Use as a Reporter Protein.

BFP can be used as a reporter protein to determine the transcription activity of a promoter, etc. A polynucleotide encoding apoprotein is fused to a target promoter or other expression control sequence (e.g., an enhancer, etc.) to construct a vector. The vector is transfected to a host cell, the coelenteramide or its analog produced by the process of the invention is brought in contact with the host cell and a calcium ion or a divalent or trivalent ion substitutable for the calcium ion. By detecting the fluorescence from the fluorescent protein of the present invention, the activity of the target promoter or other expression control sequence can be determined. As used herein, the term "contact" means that a host cell and coelenteramide or its analog as well as calcium ions or divalent or trivalent ions substitutable for the calcium ions are allowed to be present in the same culture/reaction system, and includes, for example, coelenteramide or its analog and calcium ions or divalent or trivalent ions substitutable for the calcium ions being added to a culture container charged with a host cell, a host cell being mixed with coelenteramide or its analog and calcium ions or divalent or trivalent ions substitutable for the calcium ions, a host cell being cultured in the presence of coelenteramide or its analog and calcium ions or divalent or trivalent ions substitutable for the calcium ions, and the like.

(3) Use as a Detection Marker

BFP can be used as a detection marker with its fluorescence. The detection marker of the present invention can be used to detect a target substance in, e.g., immunoassay, hybridization assay, etc. BFP can be used in the form bound to a target substance (protein, nucleic acid, etc.) in a conventional manner including chemical modifications. Detection using such a detection marker may be performed in a conventional manner.

The detection marker of the invention may also be used to determine distribution of the target substance described above, for example, by expressing the marker as a fused protein of apoprotein with the target substance, then inserting the fused protein into a cell by a technique such as microinjection, and bringing the protein in contact with coelenteramide or its analog and calcium ions or divalent or trivalent ions substitutable for the calcium ions. As used herein, the term "contact" means that a cell and coelenteramide or its analog as well as calcium ions or divalent or trivalent ions substitutable for the calcium ions are allowed to be present in the same culture/reaction system, and includes, for example, coelenteramide or its analog and calcium ions or divalent or trivalent ions substitutable for the calcium ions being added to a culture container charged with a cell, a cell being mixed with coelenteramide or its analog and calcium ions or divalent or trivalent ions substitutable for the calcium ions, a host cell being cultured in the presence of coelenteramide or its analog and calcium ions or divalent or trivalent ions substitutable for the calcium ions, and the like.

Measurement of the distribution of such a target substance may also be performed by using a detection method such as luminescent imaging. Aside from the transfection to a cell by a technique such as microinjection, the apoprotein may also be used after expression in a cell.

(4) Material for Amusement Supplies

When excited by light, BFP shows fluorescence. Therefore, BFP can be preferably used as a fluorescence material for amusement supplies. Examples of such amusement supplies are fluorescent soap bubbles, fluorescent ice bars, fluorescent candies, fluorescent color paints, etc. The amusement supplies of the invention can be prepared in a conventional manner.

3. Calcium-binding Photoprotein

As illustrated in FIG. 6, the calcium-binding photoprotein such as aequorin, etc. can be produced by reacting gFP with coelenterazine or its analog in the presence of the chelating agent such as EDTA for sequestering a calcium ion or a divalent or trivalent ion substitutable for the calcium ion.

3.1. Production of Calcium-binding Photoprotein

The calcium-binding photoprotein of the invention can be produced from the gFP of the invention. That is, the calcium-binding photoprotein of the invention can be obtained by reacting gFP with coelenterazine or its analog as a luminescence substrate.

The reaction of gFP with coelenterazine or its analog is carried out by bringing gFP in contact with coelenterazine or its analog. As used herein, the term "contact" means that the gFP of the invention and coelenterazine or its analog are allowed to be present in the same reaction system, and includes, for example, the gFP of the invention being added to a container charged with the coelenterazine or its analog of the invention, the coelenterazine or its analog of the invention being added to a container charged with the gFP of the invention, the gFP of the invention being mixed with coelenterazine or its analog, and the like.

Examples of the coelenterazine or its analog used to produce the calcium-binding photoprotein of the invention include coelenterazine, h-coelenterazine, f-coelenterazine, cl-coelenterazine, n-coelenterazine, cp-coelenterazine, ch-coelenterazine, hch-coelenterazine, fch-coelenterazine, e-coelenterazine, ef-coelenterazine, ech-coelenterazine, hcp-coelenterazine, and the like, preferably coelenterazine, h-coelenterazine and e-coelenterazine. It is described above how to make these coelenterazines and analogs thereof available.

The amount of the coelenterazine or its analog used to produce the calcium-binding photoprotein is not particularly limited, and is, e.g., 1.2 mol or more per 1 mol of gFP.

In the process of the present invention for producing the calcium-binding photoprotein, the reaction temperature and reaction time are not particularly limited and are, for example, at 0° C. to 42° C. for 0.1 to 2 hours, at 4° C. to 37° C. for 0.1 to 2 hours, or at 4° C. to 15° C. for 0.1 to 24 hours.

In a preferred embodiment of the present invention, it is preferred to carry out the invention of coelenterazine or its analog in the presence of a reducing agent. Examples of the reducing agent used herein include dithiothreitol (DTT), mercaptoethanol, etc. The amount of the reducing agent used to produce the calcium-binding photoprotein is not particularly limited, so long as the amount does not affect the regeneration, but the concentration is preferably sufficient to prevent the formation of S—S bonds by the presence of cysteine residues at the three positions of apoaequorin. Such a concentration is, for example, 1 mM dithiothreitol or 0.1% mercaptoethanol in a final concentration.

3.2. Application of Calcium-binding Photoprotein (1) Detection or Quantitative Determination of Calcium Ions The calcium-binding photoprotein of the invention is a photoprotein (holoprotein) which emits light by the action of calcium ions. Thus, the photoprotein of the invention can be used for detection or quantitative determination of calcium ions.

For the detection or quantitative determination of calcium ions, the photoprotein composed of apoprotein and a peroxide of coelenterazine analog is used. The photoprotein can be produced according to the process described above. The detection or quantitative determination of calcium ions may be performed by adding a sample solution directly to a solution of the photoprotein and measuring the luminescence generated. Alternatively, calcium ions may also be detected or quantified by adding a solution of the photoprotein to a sample solution and measuring the luminescence generated.

The detection or quantification of calcium ions may be performed by measuring the luminescence intensity of the photoprotein of the invention through the action of calcium ions, using a luminometer. Luminometers that may be used include commercially available instruments, such as the Centro LB 960 (manufactured by Berthold, Inc.). The calcium ion concentration can be quantitatively determined by preparing a luminescence standard curve for known calcium ion concentrations using the photoprotein.

(2) Bioluminescence Resonance Energy Transfer (BRET) Method

The calcium-binding photoprotein of the present invention can be used for analyses including an analysis of biological functions, an assay for enzyme activity, etc., based on the principles of intermolecular interactions by the bioluminescence resonance energy transfer (BRET) method.

For example, using the photoprotein of the invention as a donor protein and an organic compound or a fluorescent protein as an acceptor protein, the interactions between the proteins can be detected by causing bioluminescence resonance energy transfer (BRET) between them. In an embodiment of the present invention, the organic compound used as an acceptor protein is Hoechst 3342, Indo-1, DAP1, etc. In another embodiment of the present invention, the fluorescent protein used as an acceptor protein is a green fluorescent protein (GFP), a blue fluorescent protein (BFP), a mutant GFP fluorescent protein, phycobilin, etc. In a preferred embodiment of the present invention, the physiological functions to be analyzed include an orphan receptor (in particular, G-protein conjugated receptor), apoptosis, transcription regulation by gene expression, etc. Further in a preferred embodiment of the present invention, the enzyme to be analyzed is protease, esterase, kinase, etc.

Analysis of the physiological functions by the BRET method may be performed by known methods, for example, by modifications of the methods described in Biochem. J. 2005, 385, 625-637, Expert Opin. Ther Tarets, 2007 11: 541-556, etc. Assay for the enzyme activity may be performed by known methods, for example, by modifications of the methods described in Nat Methods 2006, 3:165-174, *Biotechnol J.* 2008, 3:311-324, etc.

All literatures and publications mentioned in this specification are herein incorporated in their entirety by reference into the specification, irrespective of their purposes. This specification includes all of the contents as disclosed in the claims, specification and/or drawings of Japanese Patent Application No. 2009-026757 filed on Feb. 6, 2009, which is a priority document of the present application.

The objects, characteristics and advantages of the present invention as well as the idea thereof are apparent to those skilled in the art from the descriptions given herein, and those skilled in the art can easily implement the present invention. It is to be understood that the best mode to carry out the invention and specific examples are to be taken as preferred embodiments of the present invention. These descriptions are only for illustrative and explanatory purposes and are not intended to restrict the invention thereto. It is further apparent to those skilled in the art that various modifications may be made based on the descriptions given herein within the intent and scope of the present invention disclosed herein.

EXAMPLE 1

Synthesis of Coelenteramide

4-Methoxyphenylacetyl chloride (Aldrich Inc.), 1.0 M $CH_2Cl_2$ solution in $BBr_3$ (Aldrich Inc.) and other chemical reagents used for synthesis are all commercially available and were used as they are.

Silica gel plate (MERCK Inc., Silica Gel 60 $F_{254}$, Catalogue No. 1.05715.0009) previously coated with silica gel was used as thin layer chromatography (TLC) for analysis.

Silica gel (Kanto Chemical Co., Inc., Silica Gel 60N, spherical, neutral, Catalogue No. 37563-84) was used for preparatory column chromatography.

Melting point (Mp.) was determined using YANACO MP-J3 (unadjusted). Nuclear magnetic resonance spectra (NMR spectra) at $^1$H (300 MHz) and $^{13}$C (75.5 MHz) were determined in DMSO-$d_6$ (CIL Inc.) using a Varian Gemini-300 manufactured by Varian Corp. The peak of non-deuterated dimethylsulfoxide remained in DMSO-$d_6$ as a solvent for measurements was made δ 2.49 as a standard for $^1$H NMR chemical shifts and the peak of DMSO-$d_6$ as a solvent for measurements was made δ 39.7 as a standard for $^{13}$C NMR chemical shifts, which are expressed in units of ppm, respectively. The binding constant (J) is expressed in units of Hz. Abbreviations s, m and br denote singlet, multiplet and broad, respectively. Infrared (IR) spectroscopic spectra were measured by diffuse reflectance spectroscopy on a SHIMADZU IRPrestige-21 spectrometer equipped with DRS-8000A and the absorption bands were expressed in units of cm$^{-1}$. High resolution mass spectrometry (HRMS) was performed on a mass spectrometer JEOL JMS-700 under the conditions for electron impact ionization (EI).

Synthetic Scheme for Coelenteramide

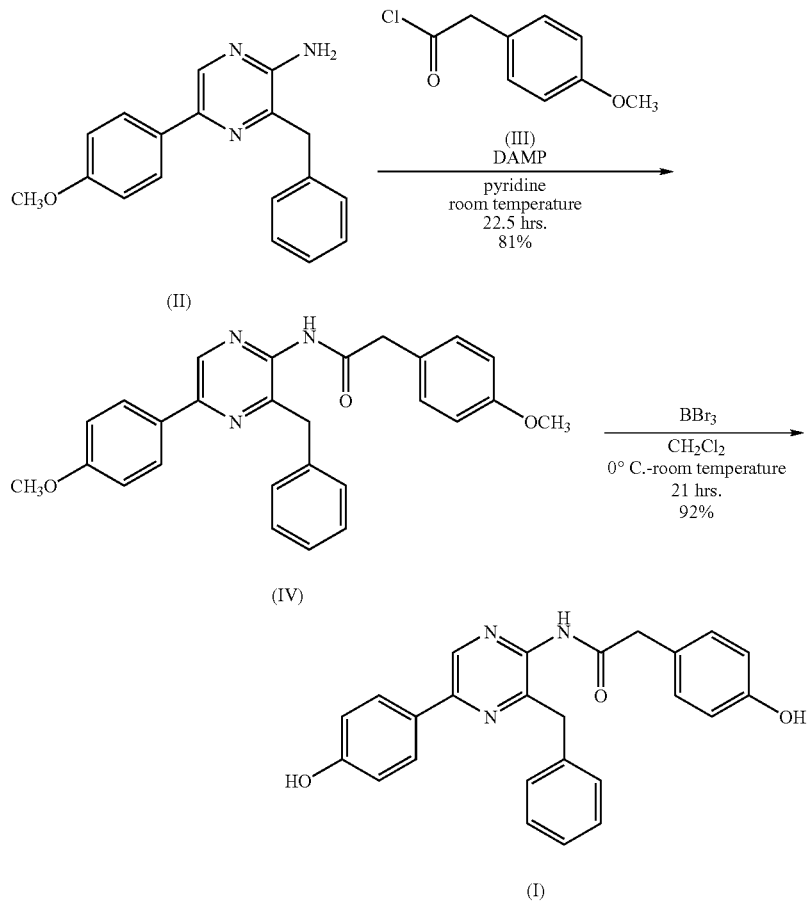

Coelenteramide Dimethyl Ether (IV)

Under an argon atmosphere, 4-(dimethylamino)pyridine (DMAP) (21.1 mg, 172 µmol) and 4-methoxyphenylacetyl chloride (III) (527 µL, 3.45 mmol) were added in this order to a solution (5 mL) of 2-amino-3-benzyl-5-(4-methoxyphenyl) pyrazine (II) (also called coelenteramine methyl ether) (Kishi et al., Tetrahedron Lett., 13, 2747-2748 (1972); Adamczyk et al., Org. Prep. Proced. Int., 33, 477-485 (2001)) (502 mg, 1.72 mmol) in pyridine. The resulting mixture was stirred at the same temperature for 22.5 hours. To this, saturated aqueous solution (100 mL) of sodium hydrogencarbonate was added and the mixture was extracted with dichloromethane (50 mL×3). The organic extract was dried over anhydrous sodium sulfate, filtered and concentrated under reduced pressure. Using toluene (20 mL×3), the remaining pyridine was azeotropically distilled off. The residue was purified on silica gel column chromatography (85 g, dichloromethane/ethyl acetate=9/1) to give coelenteramide dimethyl ether (IV) (617 mg, 81.5%) as a pale yellow solid. Recrystallization from ethyl acetate gave a colorless solid as an analytically pure sample (recrystallization twice in total gave 458 mg, 60.5%).

Mp. 189.5-191° C.; $^1$H NMR (300 MHz, DMSO-$d_6$) δ 3.61 (s, 2H), 3.73 (s, 3H), 3.80 (s, 3H), 4.03 (s, 2H), 6.88-6.93 (AA'BB', 2H), 7.02-7.07 (2×AA'BB', 4H), 7.12-7.30 (m, 5H), 8.00-8.05 (AA'BB', 2H), 8.87 (s, 1H), 10.43 (s, 1H); $^{13}$C NMR (75.5 MHz, DMSO-$d_6$) δ 41.6, 55.1, 55.3, 113.9 (2C), 114.5 (2C), 126.2, 127.5, 128.0 (2C), 128.1, 128.2 (2C), 129.0 (2C), 130.2 (2C), 137.1, 138.3, 143.7, 148.2, 150.5, 158.2, 160.7, 170.3; IR (KBr, cm$^{-1}$) 698, 833, 1034, 1177, 1256, 1495, 1514, 1543, 1672, 2833, 2957, 3265; HRMS (EI) m/z 439.1898 (M$^+$, $C_{27}H_{25}N_3O_3$ requires 439.1896).

Coelenteramide (I)

Under an argon atmosphere, a solution (20 mL) of coelenteramide dimethyl ether (IV) (660 mg, 1.50 mmol) in anhydrous dichloromethane was added to 1.0 M dichloromethane solution of boron tribromide (6.01 mL, 6.01 mmol) at 0° C. over 10 minutes. The mixture was stirred at the same temperature for 15 minutes. After the temperature was raised to room temperature, the mixture was continuously stirred for 21 hours. To this, saturated aqueous solution (100 mL) of sodium hydrogencarbonate was added and the mixture was concentrated under reduced pressure to remove dichloromethane. The remaining aqueous suspension was filtered and the solid recovered was dried in vacuum to give coelenteramide (I) (570 mg, 92.3%) as a pale yellow solid. The sample of this purity can be satisfactorily used for the production of gFP, BFP, etc.

Recrystallization from ethanol gave a colorless solid (103 mg, 16.7%) as an analytically pure sample.

Mp. 242-243° C. (dec.); $^1$H NMR (300 MHz, DMSO-$d_6$) δ 3.54 (s, 2H), 4.01 (s, 2H), 6.69-6.75 (AA'BB', 2H), 6.84-6.90 (AA'BB', 2H), 7.00-7.06 (AA'BB', 2H), 7.11-7.24 (m, 5H), 7.89-7.95 (AA'BB', 2H), 8.80 (s, 1H), 9.28 (br s, 1H), 9.85 (br s, 1H), 10.35 (s, 1H); $^{13}$C NMR (75.5 MHz, DMSO-$d_6$) δ 41.7, 115.2 (2C), 115.8 (2C), 125.7, 126.2, 126.6, 128.0 (2C), 128.2 (2C), 129.0 (2C), 130.2 (2C), 136.8, 138.4, 143.4, 148.6, 150.5, 156.2, 159.1, 170.5; IR (KBr, cm$^{-1}$) 704, 1157, 1229, 1267, 1364, 1450, 1493, 1516, 1545, 1593, 1611, 1673, 3022, 3285, 3385; HRMS (EI) m/z 411.1582 (M$^+$, $C_{25}H_{21}N_3O_3$ requires 411.1583).

EXAMPLE 2

Expression and Purification of Recombinant Histidine-tagged Apoaequorin from Bacterial Cells Recombinant histidine-tagged apoaequorin was expressed into the periplasmic space in *Escherichia coli*. The host strain used was *Escherichia coli* strain WA802 (CGSC 5610). The recombinant histidine-tagged apoaequorin expression vector, piP-His-HE, was constructed from piP-HEΔ2E (cf., Inouye & Sahara, Protein Express. Purifi. (2007) 53: 384-389).

That is, piP-HEΔ2E was digested with EcoRI and HindIII and the linker sets of histidine tag containing 6 histidine residues (SEQ ID NO: 13: 5'AAT TCC CAC CAT CAC CAT CAC CAT GGT A 3' and SEQ ID NO: 14: 5'AG CTT ACC ATG GTG ATG GTG ATG GTG GG 3') was inserted into EcoRI/HindIII site of piP-HEΔ2E to produce plasmid piP-His-HE. This plasmid contained the signal peptide sequence of the outer membrane protein A (OmpA) and 6 histidine residues under the control of lipoprotein (lpp) promoter and lac operator.

For expression of apoaequorin, the *Escherichia coli* transfected with piP-His-HE was grown in 10 ml of LB medium supplemented with ampicillin (50 μg/ml) at 30° C. for 16 hours and was added to 400 ml of LB medium containing 50 μl of antifoam (Disform CE475, Nippon Oil and Fats, Tokyo, Japan) in 3 L of a Sakaguchi flask. After culturing at 37° C. for 18 hours by reciprocal shaking (170 rpm/min), the cells were harvested by centrifugation at 5,000 g for 5 minutes from 1 L of the culture. The cells recovered were suspended in 90 ml of 50 mM Tris-HCl (pH 7.6) and then disrupted by sonication using a Branson model 250 sonifier (Danbury, Conn.). After centrifugation at 12,000 g for 20 minutes at 4° C., the resultant supernatant was applied on a nickel chelate column (Pharma Inc., 1.5×4.0 cm) equilibrated with 50 mM Tris-HCl (pH 7.6). The column was washed with 140 ml of 50 mM Tris-HCl (pH 7.6) and the adsorbed proteins containing apoaequorin were eluted with 100 ml of 50 mM Tris-HCl (pH 7.6) containing 0.1 M imidazole.

The yields of the purified products are shown in TABLE 1. From 1 L of the culture cells, 150 mg of apoaequorin was obtained.

TABLE 1

Purification of recombinant histidine-tagged apoaequorin from 1 L of culture cells using a nickel chelate Sepharose column

| Purification Step | Total Volume (ml) | Total Protein (mg)(%) | Total Luminescence Activity (×10$^{10}$ rlu) (%) | Specific Activity (×10$^8$ rlu/mg) | Purification Degree |
|---|---|---|---|---|---|
| Crude extract | 90 | 585 (100) | 8.87 (100) | 1.52 | 1.0 |
| Nickel chelate Sepharose | 10 | 150 (25.6) | 9.70 (109) | 6.47 | 4.3 |

For further purification of apoaequorin, apoaequorin (26 mg) eluted from the nickel chelate column using 0.1 M imidazole was dissolved in 5 ml of 30 mM Tris-HCl (pH 7.6) containing 10 mM EDTA and 5 mM dithiothreitol (TED buffer) and the solution was allowed to stand for 18 hours at 4° C. By adding 100 μl of 0.1 M acetic acid to the mixture, the precipitate containing white apoaequorin was formed. This white precipitate was recovered by centrifugation at 10,000×g for 10 minutes. After the resultant precipitate was dissolved again in 5 ml of TED buffer by further adding 8 μl of 25% ammonia solution, the insoluble precipitate was removed by centrifugation. The supernatant was used as purified apoaequorin.

EXAMPLE 3

Protein Analysis

Protein concentration was determined by Bradford's dye-binding assay (Anal. Biochem. (1976)72, 248-254) using a commercially available kit (Bio-Rad, California, Richmond) and bovine serum albumin (Pierce, Ill., Rockford) as a standard.

SDS-PAGE analysis was performed on a 12% separating gel under reducing conditions, as described in Laemmli (Nature (1970) 227, 680-685). As a result, it became clear that the purified apoaequorin had a purity of 95% or higher, as shown in FIG. 1.

EXAMPLE 4

Production of Synthetic BFP from Coelenteramide and Apoaequorin

Apoaequorin (0.5 mg, 22 nmol) was mixed with 10 μl of coelenteramide (1.2 μg/μl, 29 nmol, in anhydrous methanol) in 1 ml of 50 mM Tris-HCl (pH 7.6) containing 10 mM CaCl$_2$ and 1 mM DTT. The mixture was allowed to stand at 4° C. for 16 hours to produce synthetic BFP (syn-BFP). Subsequently, syn-BFP was treated at 4° C., 5,000×g for 20 minutes using centrifugal concentrator Vivaspin 2 (10,000 MWCO, Sartorius AG, Germany) to concentrate the mixture to 0.1 ml. The concentrated solution showed strong blue emission under a long wave UV lamp (366 nm).

Production of Synthetic GFP from Coelenteramide and Apoaequorin

Regarding the production of synthetic gFP (syn-gFP) from apoaequorin and coelenteramide, apoaequorin (0.5 mg, 22 nmol) was mixed with 10 μl of coelenteramide (1.2 μg/μl, 29 nmol, in anhydrous methanol) in 1 ml of 50 mM Tris-HCl (pH 7.6) containing 10 mM EDTA and 1 mM DTT. The mixture was allowed to stand at 4° C. for 16 hours to produce synthetic gFP (syn-gFP). By excitation at 335 nm, the fluorescence emission spectra shown in FIG. 2 were obtained. Formation of syn-gFP having a fluorescence capability was confirmed by apoaequorin and coelenteramide.

On the other hand, it was revealed that syn-gFP and syn-BFP could be efficiently produced in a short period of time by adding the reducing agent DTT to the solutions for producing syn-gFP and syn-BFP.

TABLE 2

Reconstitution of fluorescent proteins from apoaequorin and coelenteramide in the presence or absence of DTT and $Ca^{2+}$

| | | | Fluorescence intensity (rlu)[a] (excited at 332 nm) | |
|---|---|---|---|---|
| Incubation conditions | | Coelenteramide | 10 mM $Ca^{2+}$ ($I_{max}$, 465 nm) | 10 mM EDTA ($I_{max}$, 469.5 nm) |
| 1) | +DTT | | | |
| | 0 hr | − | 0.1 (0.3) | 0.1 (0.4) |
| | 0 hr | + | 25.4 (86.1) | 20.2 (87.4) |
| | 0.5 hr | + | 28.4 (99.1) | 22.7 (98.2) |
| | 16 hrs | + | 29.5 (100) | 23.1 (100) |
| 2) | −DTT | | | |
| | 0 hr | − | 0.1 (0.3) | 0.1 (0.4) |
| | 0 hr | + | 9.8 (33.2) | 14.8 (64.0) |
| | 16 hrs | + | 11.3 (38.3) | 18.7 (81.0) |
| | +DTT, 24 hrs | + | 22.0 (75.8) | 24.3 (105) |

[a]The reaction mixture (0.5 ml) contains apoaequorin (50 µg) and coelenteramide (1.2 µg) in 50 mM Tris-HCl (pH 7.6).

EXAMPLE 5

Measurement of Absorption and Fluorescence Spectra

Absorption spectra were measured at 25° C. with a Jasco (Tokyo, Japan) V-560 spectrophotometer (bandwidth: 0.5 nm, response, medium; scan speed, 100 nm/min.) using a quartz cuvette (10 mm light path). Also, fluorescence spectra were measured on a Jasco FP-6500 fluorescence spectrophotometer (emission/excitation bandwidth: 3 nm, response: 0.5 sec., scan speed: 1000 nm/min.).

The fluorescence spectra of syn-gFP obtained coincided with the spectra of gFP produced from aequorin, as shown in FIG. 3. As shown in TABLE 3, a ratio of 280 nm to 330 nm in the absorption spectra of the syn-BFP produced was almost the same as or higher than that of BFP produced from aequorin, indicating that it is possible to produce the equivalents.

TABLE 3

Comparison in Fluorescence Intensity between syn-BFP and BFP

| | Absorbance | | | Fluorescence Intensity[a] | |
|---|---|---|---|---|---|
| Fluorescent Protein | 280 nm (a) | 335 nm(b) | Ratio a/b | 466 nm (c) | Ratio c/b (%) |
| Syn-BFP | 1.07 | 0.20 | 5.35 | 232.5 | 1160 (100) |
| BFP[b] | 1.66 | 0.28 | 5.92 | 278.6 | 992 (85.6) |
| BFP[c] | 1.48 | 0.29 | 5.06 | — | — |

[a]excited at 335 nm
[b]BFP sample stored at 4° C. for 4 years
[c]Data dated Jul. 2, 2002 described in the literature (Inouye, *FEBS Lett.* 577 (2004) 105-110)

EXAMPLE 6

Assay for Luminescence Activity

The reaction mixture (100 µl) contained coelenterazine (0.5 µg, dissolved in 1 µl of ethanol) in 50 mM Tris-HCl (pH 7.6)-10 mM $CaCl_2$. The protein solution was added to initiate the reaction (1 µg of BFP and syn-BFP), and the luminescence intensity was recorded for 1 minute using an Atto (Tokyo, Japan) AB2200 luminometer equipped with a R4220P photomultiplier manufactured by Hamamatsu Photonics. The maximum intensity ($I_{max}$) of 1 ng of the purified recombinant aequorin showed $8.8 \times 10^5$ rlu (relative light units).

As illustrated in FIG. 4, syn-BFP produced using synthetic coelenteramide had the luminescence activities similar to those of BFP obtained from aequorin.

[Sequence Listing Free Text]

[SEQ ID NO: 1] Nucleotide sequence of natural apoaequorin

[SEQ ID NO: 2] Amino acid sequence of natural apoaequorin

[SEQ ID NO: 3] Nucleotide sequence of natural apoclytin-I

[SEQ ID NO: 4] Amino acid sequence of natural apoclytin-I

[SEQ ID NO: 5] Nucleotide sequence of natural apoclytin-II

[SEQ ID NO: 6] Amino acid sequence of natural apoclytin-II

[SEQ ID NO: 7] Nucleotide sequence of natural apomitrocomin

[SEQ ID NO: 8] Amino acid sequence of natural apomitrocomin

[SEQ ID NO: 9] Nucleotide sequence of natural apoobelin

[SEQ ID NO: 10] Amino acid sequence of natural apoobelin

[SEQ ID NO: 11] Nucleotide sequence of natural apobervoin

[SEQ ID NO: 12] Amino acid sequence of natural apobervoin

[SEQ ID NO: 13] Nucleotide sequence of histidine-tagged linker set used in EXAMPLES

[SEQ ID NO: 14] Nucleotide sequence of histidine-tagged linker set used in EXAMPLES

---

What I claimed is:

1. A process for producing a compound represented by formula (3):

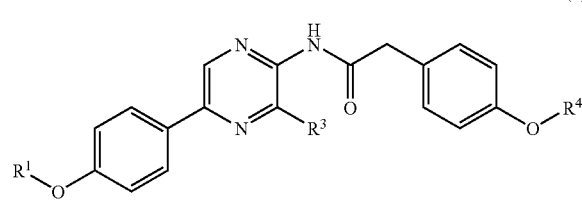

wherein,
- $R^1$ represents an alkyl having 1 to 3 carbon atoms or an arylalkyl having 7 to 10 carbon atoms,
- $R^3$ represents (i) an alkyl having 1 to 7 carbon atoms which may optionally be substituted with an alicyclic group, (ii) an alicyclic group or (iii) an arylalkyl having 7 to 10 carbon atoms, and,
- $R^4$ represents an alkyl having 1 to 3 carbon atoms or an arylalkyl having 7 to 10 carbon atoms, which comprises reacting a compound represented by formula (1):

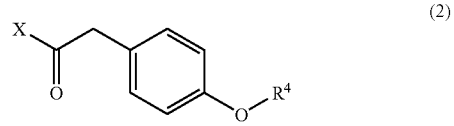

wherein $R^1$ and $R^3$ are as defined above, and, $R^2$ is amino with a compound represented by formula (2):

wherein X is a splitting-off group and $R^4$ is as defined above.

2. The process according to claim 1, wherein in formula (1), $R^1$ is methyl, ethyl, propyl, isopropyl, benzyl, α-methylbenzyl, phenethyl, 3-phenylpropyl or 4-phenylbutyl.

3. The process according to claim 1, wherein in formula (1), $R^3$ is methyl, ethyl, propyl, isopropyl, butyl, isobutyl, sec-butyl, t-butyl, pentyl, isopentyl, neopentyl, t-pentyl, hexyl, heptyl, cyclopropylmethyl, cyclobutylmethyl, cyclopentylmethyl, cyclohexylmethyl, cyclopropyl, cyclobutyl, cyclopentyl, cyclohexyl, α-methylbenzyl, phenethyl, 3-phenylpropyl or 4-phenylbutyl.

4. The process according to claim 1, wherein in formula (2), X is chlorine, bromine, iodine, methanesulfonyloxy, benzenesulfonyloxy, or toluenesulfonyloxy.

5. The process according to claim 1, wherein in formula (2), $R^4$ is methyl, ethyl, propyl, isopropyl, benzyl, α-methylbenzyl, phenethyl, 3-phenylpropyl or 4-phenylbutyl.

6. The process according to claim 1, wherein the compound represented by formula (1) is selected from the group consisting of:

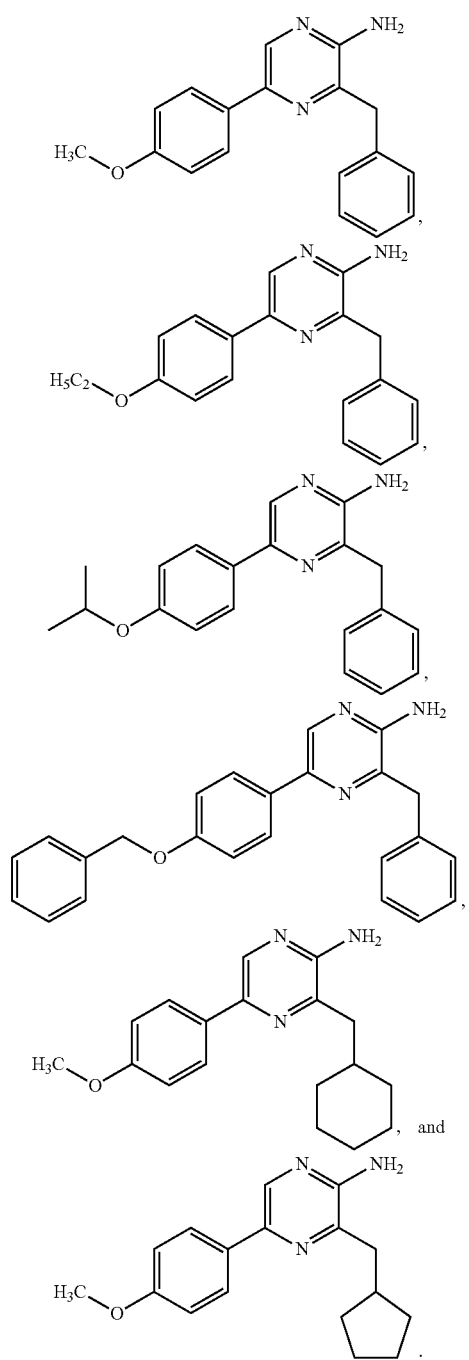

7. The process according to claim 1, wherein the compound represented by formula (2) is selected from the group consisting of:

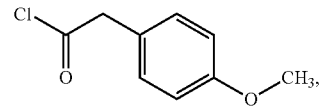

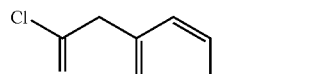

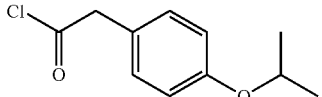

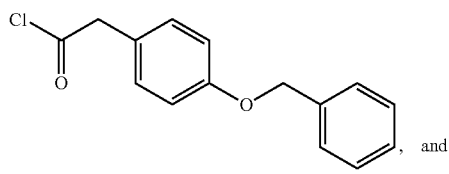

, and

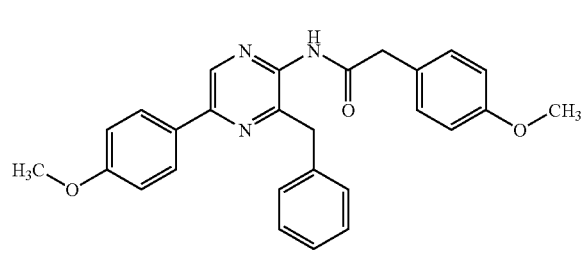

8. A process for producing the compound:

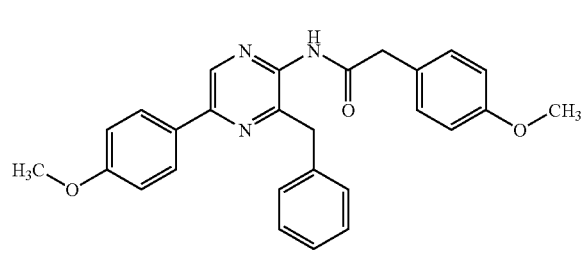

which comprises reacting the compound:

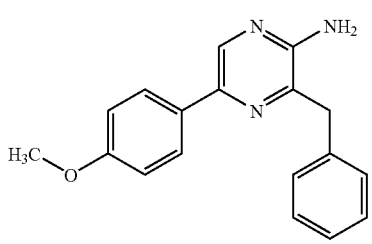

with the compound:

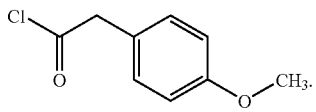

9. A process for producing a compound represented by formula (4):

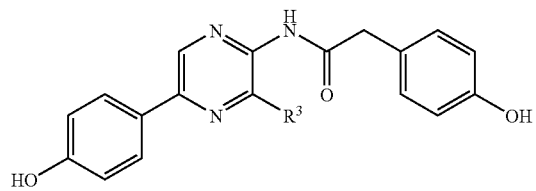

(4)

wherein $R^3$ represents (i) an alkyl having 1 to 7 carbon atoms which may optionally be substituted with an alicyclic group, (ii) an alicyclic group or (iii) an arylalkyl having 7 to 10 carbon atoms,
which comprises splitting-off a group shown by $R^1$ wherein $R^1$ represents an alkyl having 1 to 3 carbon atoms or an arylalkyl having 7 to 10 carbon atoms and a group shown by $R^4$ wherein $R^4$ represents an alkyl having 1 to 3 carbon atoms or an arylalkyl having 7 to 10 carbon atoms from a compound represented by formula (3):

(3)

wherein $R^1$, $R^3$ and $R^4$ are as defined above.

10. The process according to claim 9, wherein in formula (3), $R^1$ is methyl, ethyl, propyl, isopropyl, benzyl, α-methylbenzyl, phenethyl, 3-phenylpropyl or 4-phenylbutyl.

11. The process according to claim 9, wherein in formula (3), $R^3$ is methyl, ethyl, propyl, isopropyl, butyl, isobutyl, sec-butyl, t-butyl, pentyl, isopentyl, neopentyl, t-pentyl, hexyl, heptyl, cyclopropylmethyl, cyclobutylmethyl, cyclopentylmethyl, cyclohexylmethyl, cyclopropyl, cyclobutyl, cyclopentyl, cyclohexyl, α-methylbenzyl, phenethyl, 3-phenylpropyl or 4-phenylbutyl.

12. The process according to claim 9, wherein in formula (3), $R^4$ is methyl, ethyl, propyl, isopropyl, benzyl, α-methylbenzyl, phenethyl, 3-phenylpropyl or 4-phenylbutyl.

13. The process according to claim 9, wherein the compound represented by formula (3) is selected from the group consisting of:

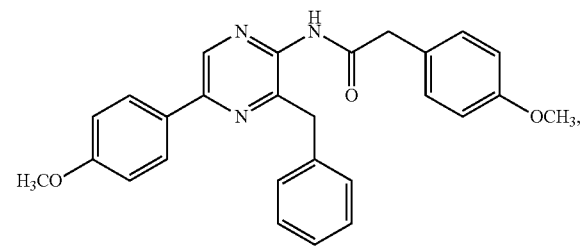
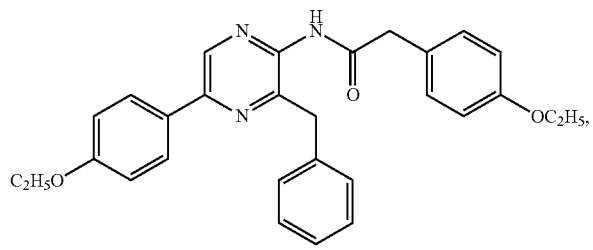
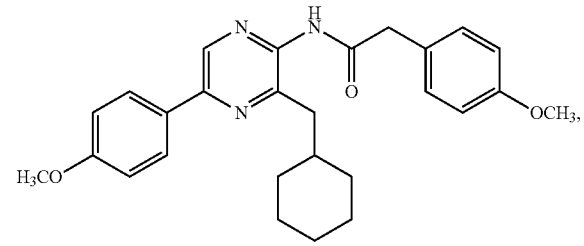
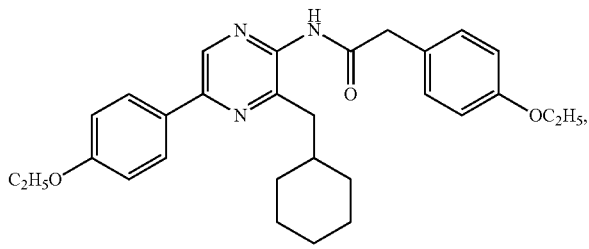
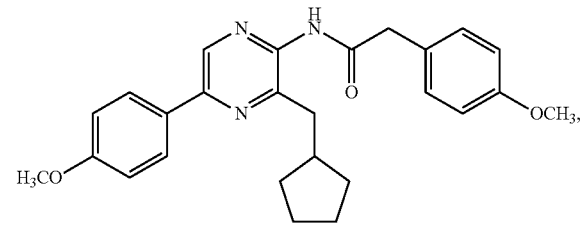
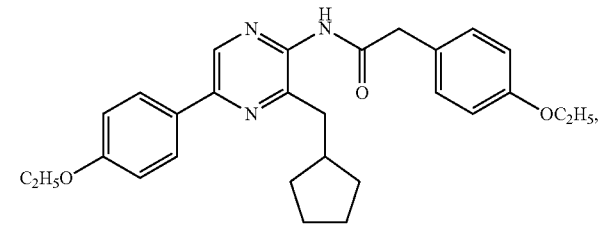
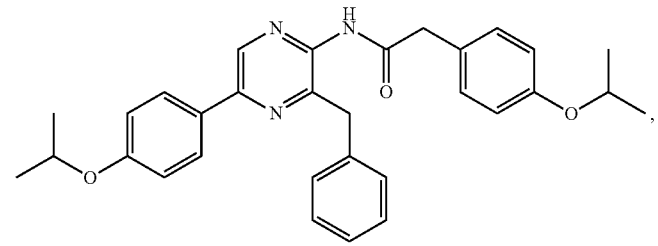

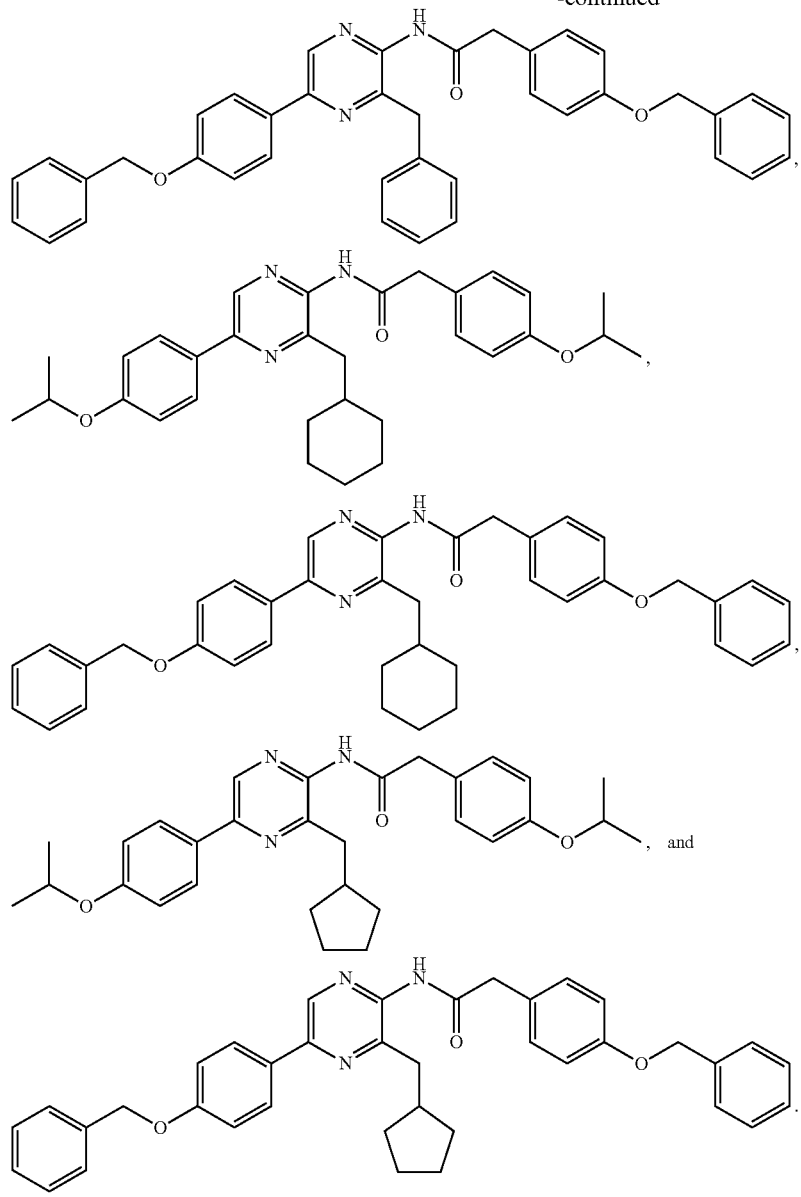
14. A process for producing the compound:
which comprises splitting-off methyl from the compound:
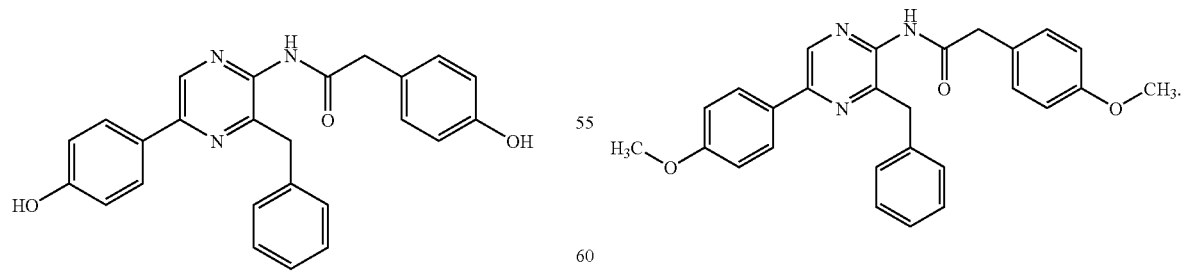
* * * * *